US005653985A

United States Patent [19]
Haigwood et al.

[11] Patent Number: 5,653,985
[45] Date of Patent: Aug. 5, 1997

[54] PURIFIED GP120 COMPOSITION RETAINING NATURAL CONFORMATION

[75] Inventors: Nancy L. Haigwood; Carl Scandella, both of Oakland, Calif.

[73] Assignee: Chiron Corporation, Emeryville, Calif.

[21] Appl. No.: 439,119

[22] Filed: May 11, 1995

Related U.S. Application Data

[62] Division of Ser. No. 240,073, May 9, 1994, which is a continuation of Ser. No. 109,002, Aug. 16, 1993, which is a continuation of Ser. No. 684,963, Aug. 20, 1991, which is a continuation-in-part of Ser. No. 490,858, Mar. 9, 1990.

[51] Int. Cl.⁶ .......................... A61K 39/21; A61K 39/12; C07K 1/00; C07K 14/00
[52] U.S. Cl. .................. 424/208.1; 424/204.1; 530/350; 530/395
[58] Field of Search .................. 424/208.1; 530/350

[56] References Cited

FOREIGN PATENT DOCUMENTS

| | | |
|---|---|---|
| 314317 | of 0000 | European Pat. Off. |
| 89/02922 | of 0000 | WIPO |
| 89/03222 | 6/1988 | WIPO |
| 91/15238 | 10/1991 | WIPO |

OTHER PUBLICATIONS

Arthur et al., "Serological Responses in Chimpanzees inoculated with Human Immunodeficiency Virus Glycoprotein (gp120) Subunit Vaccine," *Proc. Natl. Acad. Sci. USA* 84:8583–8587 (Dec. 1987).
Barrett et al., "Large–Scale Production and Purification of a Vaccinia Recombinant–Derived HIV-1 gp160 and Analysis of its Immunogenicity," *Aids Research and Human Retrovirus*, vol. 5, No. 2 (1989).
Berman et al., "Human Immunodeficiency Virus Type 1 Challenge of Chimpanzees Immunized with Recombinant Envelope Glycoprotein gp120," *Proc. Natl. Acad. Sci. USA* 95:5200–5204 (Jul. 1988).
Berman et al., "Expression and Immunogenicity of the Extracellular Domain of the Human Immunodeficiency Virus Type 1 Envelope Glycoprotein, gp160," *J. Virol.* pp. 3489–3498 (Aug. 1989).
Brown, "AIDS Vaccine Trials Viewed with Caution," *The Washington Post Newspaper*, Jun. 10, 1993.
Bulognesi, "Progress in Vaccine Against Aids," *Science*, 246:1233–1234 (1989).
Cohen, "Jitters Jeopardize AIDS Vaccine . . . ," *Science* 262:980–981.
Earl et al., "Isolate–and Group–Specific Immune Responses to the Envelope Protein of Human Immunodeficiency Virus Induced by a Live Recombinant Vaccinia Virus in Macaques," *Aids Research and Human Retroviruses*, vol. 5, No. 1 (1989).
Edelman, *Reviews of Infectious Diseases* vol. 2, No. 3 (May–Jun. 1980).

Evans et al., "An Engineered Poliovirus Chimaera Elicits Broadly Reactive HIV-1 Neutralizing Antibodies," *Nature* 339:385–388 (Jun. 1989).
Fennie et al., "Model for Intracellular Folding of the Human Immunodeficiency Virus Type 1 gp120," *J. Virol.* pp. 639–646 (Feb. 1989).
Greene, "AIDS and the Immune System," *Scientific American* pp. 99–105 (Sep. 1993).
Haynes, "Scientific and Social Issues of . . . ," *Science* 260:1279–1286.
Ho et al., "Human Immunodeficiency Virus Neutralizing Antibodies Recognize Several Conserved Domains on the Envelope Glycoproteins," *J. Virol.* pp. 2024–2028 (Jun. 1987).
Kreuter et al., *Infection and Immunity* pp. 667–675 (Feb. 1978).
Lasky et al., "Delineation of a Region of the Human Immunodeficiency Virus Type 1 gp120 Glycoprotein Critical for Interaction with the CD4 Receptor," *Cell* 50:975–985 (1987).
Littman et al., *Nature* 325:453–455 (Jan. 1987).
Maddon et al., "The Isolation and Nucleotide Sequence of a cDNA Encoding the T Cell Surface Protein T4: a New Member of the Immunoglobulin Gene Family," *Cell* 42:93–104 (Aug. 1985).
Modrow et al., *J. Virol.*, pp. 570–578 (Feb. 1987).
Nara et al., "Purified Envelope Glycoproteins from Human Immunodeficiency Virus Type 1 Variants Induced Individual, Type–Specific Neutralizing Antibodies," *J. Virol.* pp. 2622–2628 (Aug. 1988).
Palker et al., "Type–Specific Neutralization of the Human Immunodeficiency Virus with Antibodies to Env–Encoded Synthetic Peptides," *Proc. Natl. Acad. Sci. USA* 85:1932–1936 (Mar. 1988).

(List continued on next page.)

Primary Examiner—Lynette F. Smith
Attorney, Agent, or Firm—Thomas P. McCracken; Alisa A. Harbin; Robert P. Blackburn

[57] ABSTRACT

A method for purifying recombinant HIV gp120 so as to provide a glycopeptide having protein/protein binding properties substantially identical to natural viral HIV gp120, which comprises fractionating a composition containing crude gp120 sequentially using (1) ion exchange chromatography, (2) hydrophobic-interaction chromatography, and (3) size exclusion filtration, collecting at each step a fraction that exhibits specific binding affinity for CD4 peptide. The process is carried out in the absence of any affinity purification steps or any steps (such as reverse-phase HPLC) that use contact protein with organic solvents. The product obtained by this method is a purified, full-length, non-fusion recombinant HIV gp120 glycoprotein having protein/protein-interaction properties substantially identical to gp120 as presented on an HIV virus, including binding affinity for CD4 and binding affinity for at least one antibody capable of neutralizing HIV infectivity.

10 Claims, 29 Drawing Sheets

OTHER PUBLICATIONS

Putney et al., "HTLV–III/LAV–Neutralizing Antibodies to an *E. coli*–Produced Fragment of the Virus Envelope," *Science* 234:1392–1395 (1986).

Pyle et al., "Immune Response to Immunostimulatory Complexes (ISCOMs) Prepared from Human Immunodeficiency Virus Type 1 (HIV–1) or the HIV–1 External Envelope Glycoprotein (gp120)," *Vaccine* 7:465–473 (1989).

Robey et al., "Prospect for Prevention of Human Immunodeficiency . . . ", *Proc. Natl. Acad. Sci. USA* 83:7023–7027 (1986).

Scandella et al., "Purification of HIV–1 gp120 Retaining Receptor Binding Activity" Abstract Draft, First Conference on Advances in Purification of Recombinant Proteins, Interlaken, Switzerland, Mar. 14–17, 1989.

Smith et al., "Blocking of HIV–1 Infectivity by a Soluble, Secreted Form of the CD4 Antigen," *Science* 228:1704–1707.

Steimer et al., "Genetically Engineered Human Immunodeficiency Envelope Glycoprotein gp120 Produced in Yeast is the Target of Neutralizing Antibodies," *Vaccines* 87:236–241 (1987).

Steimer et al., "Recombinant Env and Gag Polypeptides in Characterizing HIV–1–Neutralizing Antibodies," *Vaccines* 88:347–354 (1988).

Strinivasan et al., *Gene* 52:71–82 (1987).

```
HXB2  MetArgValLysGluLys.........TyrGlnHisLeuTrpArgTrpGlyTrpArgTrp       17
BRU   ------------------------------------------------------Lys---       17
MN    ------------GlyIleArgArgAsn-----------...---...----------.....     16
SC    ------------GlySerGlyArgAsn--------------------------......        16
SF2   ---Lys------GlyThrArgArgAsn--------------------------......        16
NY5   ------Ala---GlyThrArgLysAsn--------------------------......        16
CDC4  ------Ala---GlyIleArgLysAsnCys-----------------------......        16
WMJ2  ------------GlyIleMetArgAsnCys------------Ile--------......        16
RF    ------Met---MetArgLysAsnCys------------------Lys-----......        16
MAL   ---------Arg---IleGlnArgAsn------AsnTrp--------------......        16
ELI   ------AlaArgGlyIleGluArgAsnCys---AsnTrp---Lys---......             16
Z6    ------AlaArg---IleGluArgAsnCysProAsn------Lys---......             16
Z3    ---------------IleGlnArgAsn---------------Lys---......             16
Z321  ---Lys------GlyIleGlnGlyAsnTrp---AsnTrp---Lys---......             16
JY1   ---------MetGlyIleArgMetAsn---------------Lys---......             16 signal peptide \/ gp120
                                   *  |       ►C1
HXB2  GlyThrMetLeuLeuGlyMetLeuMetIleCys|SerAlaThrGluLysLeuTrpValThr      37
BRU   -----------------Ile-------------|----------------------------      37
MN    -----------------Leu-------------|----------------------------      36
SC    -----------------Ile-------------|------Ala---Gln-------------      36
SF2   ------Leu------------------------|----------------------------      36
NY5   ---------------------------------|------Ala---Gln-------------      36
CDC4  ---------------------------------|------AlaAlaAsn-------------      36
WMJ2  --------------Phe------Trp-------|------Val---Gln-------------      36
RF    ---------------------------------|------Ala---Asp-------------      36
MAL   ---Met------------------Thr------|---IleAla---Asp-------------      36
ELI   ---Ile---------Ile------Thr------|------AlaAspAsn-------------      36
Z6    ---Ile---------Ile---------------|------AlaAspAsn-------------      36
Z3    SerLeuIleIle----------Ile--------|Lys---Ile------Ser----------      36
Z321  ------LeuIle------LeuValIle------|------Ala---Asn-------------      36
JY1   ---Ile---------Ile------Thr------|---ValAla---Asp-------------      36
```

FIG. 2A

```
         *
HXB2  ValTyrTyrGlyValProValTrpLysGluAlaThrThrThrLeuPheCysAlaSerAsp    57
BRU   ------------------------------------------------------------    57
MN    ------------------------------------------------------------    56
SC    ------------------------------------------------------------    56
SF2   ------------------------------------------------------------    56
NY5   ------------------------------------------------------------    56
CDC4  ------------------------------------------------------------    56
WMJ2  ------------------------------------------------------------    56
RF    ---------------------------------------------------------Glu    56
MAL   ------------------------------------------------------------    56
ELI   ------------------------------------------------------------    56
Z6    ------------------------------------------------------------    56
Z3    ---------------------------Asp---Glu------------------------    56
Z321  ---------------------------Asp---Glu------------------------    56
JY1   ------------------------------------------------------------    56

*
HXB2  AlaLysAlaTyrAspThrGluValHisAsnValTrpAlaThrHisAlaCysValProThr    77
BRU   ------------------------------------------------------------    77
MN    ---------------------------------------Gln------------------    76
SC    ------------------------------Ile---------------------------    76
SF2   ---Arg------------------------------------------------------    76
NY5   ------------------------------------------------------------    76
CDC4  ------------------------------Ala---------------------------    76
WMJ2  ------------Ser------Ala------------------------------------    76
RF    ------------Lys---------------------------------Lys---------    76
MAL   ------Ser---Glu---------------Ile---------------------------    76
ELI   ------Ser---Glu---------Ala---Ile---------------------------    76
Z6    ------Ser---Lys---------Ala---Ile---------------------------    76
Z3    ------------GluLys---Ser---------------------------------Ser    76
Z321  ---------------------Lys------------------------------------    76
JY1   ------Ser---GluPro---Ala------Ile---------------------------    76
```

FIG. 2B

```
                                     [        ]
HXB2  AspProAsnProGlnGluValValLeuValAsnValThrGluAsnPheAspMetTrpLys         97
BRU   ------------------------------------------Asn---------                97
MN    ---------------Glu------------------------Asn---------                96
SC    ------------------Gly---------------------Asn---------                96
SF2   ------------------Gly---------------------Asn---------                96
NY5   ------------------Gln---------------------Asn---------                96
CDC4  Asn---------------Glu---------------------Asn---------                96
WMJ2  ---------------Ile---Gly------------------Asn---------                96
RF    ---------------Leu---Glu------------------Asn---------                96
MAL   ------------IleGlu---Glu------------Gly---Asn---------                96
ELI   ------------IleAla---Glu------------------Asn---------                96
Z6    ------------IleGlu---Glu------------------Asn------Arg                96
Z3    ------Ser---------Leu------Gly------------Asn---------                96
Z321  ------------------LeuSer---Gly---------Lys------------                96
JY1   ------------Arg---IleGluMetGlu------------Asn---------                96

HXB2  AsnAspMetValGluGlnMetHisGluAspIleIleSerLeuTrpAspGlnSerLeuLys         117
BRU   ------------------------------------------------------               117
MN    ---Asn------------------------------------------------               116
SC    ---Asn------------------------------------------------               116
SF2   ---Asn------------Gln---------------------------------               116
NY5   ---AsnThr---------------------------------------------               116
CDC4  ---Asn------------------------------------------------               116
WMJ2  ---Asn------------------------------------------------               116
RF    ---Asn------------------------------------------------               116
MAL   ---Asn------------------------------------------------               116
ELI   ---Asn------------------------------------------------               116
Z6    ---Asn------------Ile---------------------------------               116
Z3    ---Lys------------------------------------------------               116
Z321  ---Asn------------------------Val---------------------               116
JY1   ---Asn--------------------------------------Asn-------               116
```

FIG. 2C

```
                              C1◄──────►D1
             *                *      *
HXB2  ProCysValLysLeuThrProLeuCysValSerLeuLysCys ThrAspLeuLys......    135
BRU   ---------------------------------------- ---------Gly------    135
MN    ---------------------------------------- Thr---Asn---------Arg------    134
SC    ---------------------------------------- Thr---Asn---Asn---Arg------    134
SF2   ---------------------------------------- Thr---Asn---------GlyLys---    135
NY5   -------------Ser------------------------ Thr---Asn---------Thr------    134
CDC4  ---------------------------------------- Thr---Asn---------AsnThr---    135
WMJ2  ---------------------------------------- Thr---Asn---Ile---Lys...------    133
RF    ---------------------------------------- Thr---Asn------AlaAsnLeu---    135
MAL   ---------------------------------------- Thr---Asn---AsnVal...------    133
ELI   ---------------------------------------- Thr---Asn---Ser---GluLeuArg---    135
Z6    ---------------------------------------- Thr---Asn---------GluSerAspGlu    136
Z3    -------------Phe------------------------ Thr---Asn---Ile---Val--------    134
Z321  ---------------------------------------- Thr---Ser---HisAsnIleThrIleLys    136
JY1   ---------------------------------------- Thr---Asn------AsnAlaGlyGly---    135

[       ]        [         ]
HXB2  ........AsnAspThr....AsnThrAsnSerSer...............Ser    144
BRU   ------------Ala--------------------------AsnThrAsnSerSer---    149
MN    ------------Thr-----------------Asn---ThrAlaAsnAsnAsn---------    148
SC    ----------------------Ser------AlaThr------AsnThrThrSerSerAsn    148
SF2   -----------...Ala------------------------AsnTrpLys------...    145
NY5   ------------Ala---TyrAla...---Gly----------------------...    142
CDC4  ------------Asn------...-----ThrThrGluLeuSerIleIleValVal...    149
WMJ2  ------------Ile---AspTrpLys---ThrThr----------IleIle------...    144
RF    ------------Gly------...,,,---ValThr----------SerSer---    144
MAL   ------------Gly---AlaVal...---GlyThrAsnAlaGlySerAsnArgThrAsn    149
ELI   ------Asn---Gly---MetGlyAsn---ValThr----------------...    145
Z6    TrpMetGly---Val---GlyLys...---ValThr----------------...    147
Z3    ------------Ser----------...---AsnThr----------------...    141
Z321  Asp---------Asn----------...,ValAspThr----------------...    144
JY1   ------------Lys---Thr---Gly---AsnThr-------------ThrAsnGln    147
                          [   *   ]  [      ]
```

FIG. 2D

```
                                                     D1◄──  *  ──►D2
                                                       [    |    ]  [              ]
HXB2   GlyArgMetIleMetGluLys...GlyGluIleLysAsnCysSerPheAsnIleSerThr    163
BRU    ---Glu---Met------------------------------------------------    168
MN     AsnSerGluGlyThrIle---Gly------Met---------------------Thr---    168
SC     ArgGly...Lys------Gly---------MetThr------------------Thr---    166
SF2    ......GluGlu...Ile-----------------------------------Thr---     161
NY5    ...SerGluGluArg......-------------Arg-------------ValThr---     158
CDC4   ...TrpGluGlnArgGly------------MetArg------------------Thr---    167
WMJ2   ..................GlyGly------Val--------------------Thr---    158
RF     ---GlyThrMet------Asn------------------------GlnValThr---       163
MAL    AlaGluLeuLys------Ile---------Val--------------------ThrPro    168
ELI    ...ThrGluGlu.......---Gly......Met--------------------ValThr--- 160
Z6     ......GluAspIleArg...---......Met----------------------Thr---   161
Z3     ......GluGluAlaThr...---......---Thr--------LysValPro---        155
Z321   ............GluMet------Glu----------------Tyr---MetThr---      159
JY1    GluGluGlnMet---------------Met----------------------Thr---      166

HXB2   SerIleArgGlyLysValGlnLysGluTyrAlaPhePheTyrLysLeuAspIleIlePro    183
BRU    -----------------------------------------------------------     188
MN     ---------Asp---Met------------------Leu Leu---------------ValSer 188
SC     ---------Ser------------------------Leu-------------------ValVal--- 186
SF2    ---------Asp---Ile----------Asn---Leu---ArgAsn------ValVal---  181
NY5    Ile------Asn---Ile----------------Leu------Arg----------Val--- 178
CDC4   ---------Asp----------Arg---------Leu-------------------ValGlu--- 187
WMJ2   ---Arg---Asp----------His---------Leu-------------------ValVal--- 178
RF     ---Arg---Asp---Thr----Lys---------Leu-------------------ValVal--- 183
MAL    ValGlySerAsp---Arg---,,,------Thr------Asn------LeuValGln       187
ELI    ValLeuLysAsp---Lys---GlnVal------Leu---Arg---------Val---       180
Z6     ValVal---Asp---ThrLysGlnValHis---Leu---Arg---------Val---       181
Z3     GluLeuLysAsp---ThrGluThrValHisThrLeu-------------ValVal---      175
Z321   GluLeu---Asp---GlnArg---Ile---SerLeu------Arg------Val---       179
JY1    Val---SerAsp---LysLysGlnValHis---Leu------Arg------ValVal---    186
```

FIG. 2E

```
                           [        ]     "peptide T" region
       HXB2  Ile................AspAsnAspThr.......................Thr      189
       BRU   ---------------------------------------------------------      194
       MN    -------------------------------Ser-----------------------      194
       SC    ----------------------------.....-----------------------      190
       SF2   ---------------------------AlaSer--------ThrThrThrAsnTyr---   192
       NY5   ----------AspLys------------.....-----------------------      184
       CDC4  ----------Asp----------LysAsn------------ThrThrAsnAsn---      198
       WMJ2  ----------LysGly------AsnSer----------------------Ser         186
       RF    ----------GluLysGly...---IleSerProLysAsnAsnThrSerAsnAsn---    199
       MAL   ---AspAspSer---------------.....----------------------Ser     194
       ELI   ----------------------------Ser------SerThrAsnSer--------    190
       Z6    ----------------------------Asn------SerThrAsnSer--------    191
       Z3    Leu--------------------...---Val---AsnAsnSerSerIleSer------Ser  186
       Z321  ---GlyGly-----------------...---.....-----SerSerAsnGlyAspSerSer  190
       JY1   ---AspAspAspAsnSerAla...---ThrSer---Asn---------ThrAsnTyr---   201

D2 ←――→ C2
                                  * [                      ]            *
       HXB2  SerTyrSer.........LeuThrSerCysAsnThrSerValIleThrGlnAlaCysPro  206
       BRU   ------Thr-----------------------------------------------      211
       MN    ------Arg------------Ile---------------------------------    211
       SC    ------Thr------------IleAsn------------------------------    207
       SF2   Asn---Arg------------IleHis-------Arg--------------------    209
       NY5   ------Thr------------IleAsn------------------------------    201
       CDC4  Lys---Arg------------IleAsn------------------------------    215
       WMJ2  Arg---Arg------------IleAsn------------------------------    203
       RF    ------GlyAsnTyrThr---IleHis-------Ser--------------------    219
       MAL   ------Arg------------IleAsn------------------------------    211
       ELI   Asn---Arg------------IleAsn------------Ala---------------    207
       Z6    Asn---Arg------------IleAsn------------Ala---------------    208
       Z3    Thr---Arg------------IleAsn------------Thr---------------    203
       Z321  Lys---Arg------------IleAsn------------Ala---------------    207
       JY1   Asn---Arg------------IleAsn------------Ala---------------    218
```

FIG. 2F

```
HXB2  LysValSerPheGluProIleProIleHisTyrCysAlaProAlaGlyPheAlaIleLeu   226
BRu   ------------------------------------------------------------   231
MN    ---Ile------------------------------------------------------   231
SC    ---------------------------------------------ArgTrp...------   226
SF2   ---------------------------------------Thr------------------   229
NY5   ------------------------------------------------------------   221
CDC4  ---------------------------------------Thr---Thr---------Leu---  235
WMJ2  ------------------------------------------------------------   223
RF    ---------------------------------------Thr------------------   239
MAL   ------Thr---Asp---------------------------------------------   231
ELI   ------------------------------------------------------------   227
Z6    ------------------------------------------------------------   228
Z3    ------------------------------------------------------------   223
Z321  ------------------------------------------------------------   227
JY1   ------Thr---------------------------------------------------   238

HXB2  LysCysAsnAsnLysThrPheAsnGlyThrGlyProCysThrAsnValSerThrValGln   246
BRU   ------------------------------------------------------------   251
MN    ---------Asp---Lys----Ser----Lys---Ser---Lys----------------   251
SC    Asn---------Lys---------------------------------------------   246
SF2   ---------------------------Lys------------------------------   249
NY5   ---------Asp---Lys------------------------------------------   241
CDC4  ---------Asp---Lys------------------------------------------   255
WMJ2  ---------Asp---Lys------------------------------------------   243
RF    ---------Asp---Lys---------------------Lys------------------   259
MAL   ---------Asp---Lys----------GluIle---Lys--------------------   251
ELI   ------ArgAsp---Lys------------------------------------------   247
Z6    ------ArgAsp---Arg------------------------------------------   248
Z3    ---------Asp---Lys---------------------Lys------------------   243
Z321  ------ArgAspGluGlu---Glu---Lys---------Arg------------------   247
JY1   ------LysAsp---Lys---------------------LysLys---------------   258
```

FIG. 2G

```
        *                                              [                  ]
HXB2  CysThrHisGlyIleArgProValValSerThrGlnLeuLeuLeuAsnGlySerLeuAla          266
BRU   ----------------------------------------------------------            271
MN    ----------------------------------------------------------            271
SC    ------------------------------------His-------------------            266
SF2   ------------------------------Ile-------------------------            269
NY5   -----------------Lys--------------------------------------            261
CDC4  ----------------------------------------------------------            275
WMJ2  ----------------------------------------------------------            263
RF    ----------------------------------------------------------            279
MAL   -----------------Lys--------------------------------------            271
ELI   ----------------------------------------------------------            267
Z6    ----------------------------------------------------------            268
Z3    -------------------------------------------------------Ser            263
Z321  ----------------------------------------------------------            267
JY1   ----------------------------------------------------------            278

[     ]
HXB2  GluGluGluValValIleArgSerValAsnPheThrAspAsnAlaLysThrIleIleVal           286
BRU   ---------------------------Ala------------------------------         291
MN    ---------------------------Glu------------------------------         291
SC    ------------------Leu------Glu------------------------------         286
SF2   ---------------------------Asp---------Asn------------------         289
NY5   ---Gly---------------------Glu---------Asn------------------         281
CDC4  ---------------------------Glu---------Asn------------------         295
WMJ2  ---------Ile---------------Glu------------------------------         283
RF    ---------------------------Glu------------Val---------------         299
MAL   ---------IleMet------------Glu---Leu------Thr---Asn---------         291
ELI   ------------Ile------------Glu---Leu---Asn---Asn------Ala---         287
Z6    ---------IleIle------------Glu---Leu---Asn---------Ile------         288
Z3    ------------Ile------------Glu---Ile---Asn------------------         283
Z321  ---Gly-------Arg-----------Glu---------------------Ile------         287
JY1   ---------IleIle------------Glu---Leu---Asn---Val------------         298
```

FIG. 2H

```
           C2◄──┐                    ┌──►D3
                [          ]    [ *  ]                     [              ]
HXB2  GlnLeuAsnThrSerValGluIleAsnCysThrArgProAsnAsnAsn...ThrArgLys         305
BRU   ------|---Gln---------------|-----------------------------------     310
MN    His---|---Glu------Gln------|------------Tyr-------Lys-------        310
SC    ------|-LysGluAla-----------|-------------------------ThrArg         305
SF2   ------|---Glu------Ala------|-----------------------------------     308
NY5   ------|---Lys----------------|------------------------------Lys---   300
CDC4  ------|---Val----------------|-------------His-----------------      314
WMJ2  His---|---Glu----------------|------------Tyr---------Val---Arg      302
RF    ------|---Ala------Gln-------|-----------------------------------    318
MAL   ------|---GluThr---Thr-------|------------Gly----------------Arg     310
ELI   His---|---Glu------Lys---Thr---Ala------TyrGln-------------Gln       306
Z6    ------|---Glu------Ala---Ala-|-----------TyrLys-------------Gln      307
Z3    ------|---GluThr---Lys-------|-----------GlySerAsp---LysLysIle       302
Z321  ------|-ValLysPro---Asn---Thr---Met-------------------------         306
JY1   His---|---Glu------------------|----------Asp---LysIle------Gln      318

HXB2  Arg.........IleArgIleGlnArgGlyProGlyArgAlaPheValThrIleGlyLys          322
BRU   Ser---------------------------------------------------------          327
MN    -----------------His---.....,---------------Tyr----ThrLysAsn          325
SC    Ser--------------His---.....,---------------TyrAlaThr---Asp           320
SF2   Ser--------------Tyr---.....,---------------His---Thr---Arg           323
NY5   Gly--------------Ala---.....,---------------ThrLeuTyrAlaArgGlu---     315
CDC4  ---ValThrLeu...........,-----------------ValTrpTyr---Thr---Glu        329
WMJ2  Ser------------LeuSer---.....,--------------------Arg---Arg...Glu     316
RF    Ser------------ThrLys...........,-----------ValIleTyrAlaThr---Gln     333
MAL   Gly------------HisPhe......,--------Gln---LeuTyr---Thr---...          324
ELI   --------------ThrPro---.....,---Leu---GlnSerLeuTyr---ThrArgSer        321
Z6    Ser-----------ThrPro---.....,---Leu---Gln---LeuTyr---ThrArgGly        322
Z3    --------------GlnSer---ArgIle-----------LysVal---TyrAlaLys---Gly      319
Z321  Ser-----------Ser---.....,------------------PheAlaThr---Asp           321
JY1   Ser-----------ThrPro---.....,---Leu---Gln---LeuTyr---ThrArg...        332
```

FIG. 21

```
                                     D3
                                       * [           ]
HXB2  ...........IleGlyAsnMetArgGlnAlaHisCysAsnIleSerArgAlaLysTrp    338
BRU   ---------------------------------------------------------     343
MN    ---------Ile------ThrIle-------------------------------------  342
SC    ---------Ile------AspIle-------------------------------------  337
SF2   ---------Ile------AspIle---Lys-----------------------Gln---    340
NY5   ---------Ile------AspIle-----------------------Lys----------   332
CDC4  ---------IleLeu-------Ile----------------------------Gln---    346
WMJ2  ---------Ile------IleIle-------------------------------------  333
RF    ---------Ile------AspIle---Lys---------Leu-----------Gln---    350
MAL   ---------IleVal---AspIle---Arg---Tyr---Thr---AsnGluThrGlu---   341
ELI   Arg---SerIle----------.........------------------------Gln--- 337
Z6    ArgThrLysIle----------.........----------------LysGluAsp---    339
Z3    ---------IleThr---...----------------------ThrAspGlyGlu---     333
Z321  ---------Ile------AspIle---------------Val------ThrGlu---      338
JY1   ---------IleLys---AspIle---------Tyr-----------Ala---Ala---    349

[        ]                                              [
HXB2  AsnAsnThrLeuLysGlnIleAspSerLysLeuArgGluGlnPheGlyAsnAsn...Lys   357
BRU   ---Ala---------------Ala--------------------------------       362
MN    ---Asp-------Arg-------Val-----------Lys----------Lys---...--- 360
SC    --------------------ValIle---------Asp------Glu---...------    355
SF2   -------------Glu------ValLys--------------------------------   359
NY5   ---Asp-----------------ValThr--------Lys----------Arg---...--- 350
CDC4  ----------------Gln-------AlaThrThr---------------------...    364
WMJ2  --------------------ValGlu--------------------Lys---...------  351
RF    ------------------ValValThr-----------------Asp---...          368
MAL   AspLys------Gln---ValAlaVal------GlySerLeuLeuAsnLysThr---...   359
ELI   SerLys------Gln---ValAlaArg------GlyThrLeuLeuAsnLysThr---...   355
Z6    ---Lys------GlnArgValAlaIle------GlyAsnLeuLeuAsnLysThr---...   357
Z3    Arg---------Gln---ValAlaIleAla------Arg------Asn---...------   351
Z321  ---Asp------SerLysValAlaAlaGln------LysHis---Val---ThrSerThr   358
JY1   ---Lys------Gln---ValAlaLys------GlyAspLeuLeuAsnGlnThr---...   367
```

FIG. 2J

```
                            ]        ┌──►C3
HXB2  ThrIleIlePheLysGln SerSerGlyGlyAspProGluIleValThrHisSerPheAsn    377
BRU   ------------------ ------------------------------------------    382
MN    ------Val---Asn--- --------------------------Met------------    380
SC    ------------AsnArg --------------------------Met------------    375
SF2   ------Val---Asn--- --------------------------Met------------    379
NY5   ------Val---Asn--- --------------------------Met------------    370
CDC4  ------Ala---Asn--- --------------------------Met------------    384
WMJ2  ------Val---AsnHis ------------------------------------------    371
RF    ------Val---ThrSer --------------------------Leu------------    388
MAL   Lys---------AsnSer --------------------------Thr------------    379
ELI   Ile---Lys------Pro --------------------------Thr------------    375
Z6    ------------Pro    ------------Ala-----------Thr------------    377
Z3    Ser---------AsnSer ------------Ile-----------Thr-------Thr---   371
Z321  Asp---------AlaAsn ------------Val-----------Thr------------    378
JY1   ---------ProProAla --------------------------Thr------------    387

C3 ◄──┐ ┌──► D4
       *           *  [         ]      [           ]
HXB2  CysGlyGlyGluPhePheTyrCys AsnSerThrGlnLeuPheAsnSerThrTrp......    395
BRU   ----------------------- -----------------------------------     400
MN    ----------------------- ---ThrSerPro--------------------------  398
SC    ----------------------- --------------------Ser---------------  393
SF2   ---Arg----------------- ---Thr--------------Asn---------------  397
NY5   ----------------------- LysThr-----------------------------     388
CDC4  ----------------------- ------------------------Ala-------Asn   403
WMJ2  ----------------------- -----------------------------------     389
RF    ----------------------- ---Thr-----------------------------     406
MAL   ---Arg----------------- ---ThrSerLys-----------------------     397
ELI   ----------------------- ---ThrSerGly-----------------------     393
Z6    ----------------------- ---ThrSerGly-----------------------     395
Z3    ----------------------- ---ThrSerGlu------ThrGlyIle---------    389
Z321  ----------------------- ---ThrSerGly---------Gly------LeuAsn    398
JY1   ----------------------- ---ThrSerArg-----------------------     405
```

FIG. 2K

```
         [        ]               [            ]
HXB2  ......PheAsnSerThr...TrpSerThr.........GluGlySerAsnAsnThrGlu    409
BRU   ---------------------------------------------------------------  414
MN    ---AsnGly---Asn---------AsnAsnThrThr---,,,------------Asn,,,     413
SC    ------,,,---Gly------,,,,,,,,,------------------------------Gly  403
SF2   ---ArgLeu---His------------,,,,,,,,,--------------,,,,,,,,,---Lys 406
NY5   ---Leu------------------AsnAsp------Thr---Arg---,,,,,,,,,,Asp   401
CDC4  ValThrSer---Gly------------,,,,,,,------------,,,,,,---ValThrArgLys 415
WMJ2  ------,,,---Gly---Asp.........,------IleLys---Asp---LysAsn,,,   400
RF    ----------------------------,,,,,,,,,----------------------Gly  416
MAL   ---GlnAsn---GlyAlaArg.........,,,,,,,------,,,Leu------Ser------ 409
ELI   ------,,,---IleSerAla---AsnAsnIleThr---,,,Glu---------SerThr    408
Z6    ---AsnIle---AsnSer---.........,------------------Ala---Ser------ 407
Z3    ------,,,---Gly---------AspLysAsnCys---,,,,,,,,,ThrSer------    401
Z321  GlyThrSer---Asn---------LysIleAspThr---,,,,,,,,,,,,,,,,,,,,     409
JY1   ------------SerThr---AsnAsnAspThr---,,,,,,,,,Leu---Ser---       418

D4 ----->C4
                                  *
HXB2  GlySerAspThr.........IleThrLeuProCysArgIleLysGlnIleIleAsnMet    426
BRU   ---------------------------------Phe---------                   431
MN    ,,,,,,,,,,,-------------------Gln---Lys----------------------   426
SC    ---Asn----------------------------------Glu------------------   420
SF2   ---Asn--------------Ile--------------------------------------   423
NY5   AsnAsnGlu-----------IleIle-----------------------------------Ser 418
CDC4  GlnLys------GlyAspIle----------------------------------------Arg 435
WMJ2  ,,,,,,Ser---Leu----------------------------------------------   416
RF    ---Asn-------------------------------------------------Val----- 433
MAL   SerThrGlySer-------------------------------------------------   426
ELI   AsnThrAsn,,,---------------Gln-------------------------Lys---   424
Z6    SerAspAsnLysLeu------------Gln-------------------------------   425
Z3    SerAsnCys---GlyAsn-------------------------------------ValValArgThr 420
Z321  ValAsn--------------Ile--------------------------------Val----- 426
JY1   ---Thr,,,,,,-------Lys---------------------------------------   433
```

FIG. 2L

```
              --- CD4 binding region ---                              *
HXB2  TrpGlnLysValGlyLysAlaMetTyrAlaProProIleSerGlyGlnIleArgCysSer    446
BRU   ------Glu---------------------------------------------------    451
MN    ------Glu------------------------------Glu-------------------   446
SC    ------Glu------------------------------Lys------ValLys------    440
SF2   ------Glu------------------------------Gly---------Ser------   443
NY5   GlyArg---+++                                                    422
CDC4  ------Val---------------------Leu------Lys---Leu------------   455
WMJ2  ------Gly------------------------------Gln-------------------   436
RF    ------Glu---------------------------------------Lys---Ile      453
MAL   ---------Thr---------------------------Ala---Val---Asn---Leu   446
ELI   ValAlaGlyArg...------Ile---------------GluArgAsn---Leu------   443
Z6    ------Gly------------------------------Glu---------Asn------   445
Z3    ------Gly------Gln---------------------Glu---Thr------------   440
Z321  ------Arg------Gln---------------------Lys---Val---Lys---Val   446
JY1   ------Gly------------------------------Glu---Leu---Lys---Thr   453

C4 ◄──┬──► D5
         [        ]
HXB2  SerAsnIleThrGlyLeuLeuLeuThrArgAspGlyGly............│...AsnSer   461
BRU   ----------------------------------------------------│------Asn   466
MN    ---------------------------------------LysAspThrAsp              463
SC    ---------------------------------AsnSerLysAsnGlySerLys           460
SF2   ------------------------------------------Thr---Val              459
NY5
CDC4  ---------------------------------Gly----------│---...Glu         470
WMJ2  ---------------------------------AsnSer-------│---......          451
RF    ----------------------------------------------┤GluAspThr          469
MAL   ------------Ile------------------AsnSer-------│---SerAsp          463
ELI   ----------------------------------------------│---IleAsn          458
Z6    ----------------------------------------------┤---ThrAsn          460
Z3    ---------------------------------AsnGlyLysCysAsnSerLys            460
Z321  ------------Ile------------------ValGly-------│---...Asn          461
JY1   ---------------------------------Val----------│---...Asn          468
```

FIG. 2M

```
            D5           C5
          [    ]
HXB2  AsnAsnGluSer GluIle PheArgLeuGlyGlyGlyAspMetArgAspAsnTrpArgSer   481
BRU   ------Gly---  -----  ---Pro------------------------------------  486
MN    Thr---AspThr  -----  ---Pro------------------------------------  483
SC    ---GluAsnThr  -----  ---Pro------------------------------------  480
SF2   Thr---AspThr  ---Val ---Pro------------------------------------  479
NY5
CDC4  ---GlnThrThr  -----  ---Pro------------------------------------  490
WMJ2  SerSerArgGlu  -----  ---Pro---------Asn------------------------  471
RF    Thr---ThrThr  -----  -----------------Asn----------------------  489
MAL   ---SerAspAsn  ---ThrLeu ---Pro---------------------------Ile---  483
ELI   ---SerThrAsn  ---Thr  ---Pro-----------------------------------  478
Z6    ---SerSerAsn  ---Thr  ---Pro-----------------------------------  480
Z3    +++                                                              461
Z321  ---ThrSerAsn  ---Thr  ---Pro-----------------------------------  481
JY1   ---SerThrAsn  ---Thr  ---Pro-----------Lys----------------Asn    488

HXB2  GluLeuTyrLysTyrLysValValLysIleGluProLeuGlyValAlaProThrLysAla     501
BRU   ------------------------------------------------------------     506
MN    ---------------------------Thr------------------------------     503
SC    ------------------------------------------------------------     500
SF2   ---------------------Ile------------------Ile---------------     499
NY5
CDC4  ------------------------------------------------------------     510
WMJ2  ---------------------Arg------------------------------------     491
RF    ---------------------Arg--------------------------------Arg---   509
MAL   ---------------------Arg------------------------------------     503
ELI   ---------------------Gln--------------------------------Arg---   498
Z6    ------------------------------------------------------------     500
Z3
Z321  ------------------------------------------------------------     501
JY1   ---------------------Arg------------------Ile---------Arg---     508
```

FIG. 2N

```
                    gp120 C5◄──┬──►gp160 C5 (to end)
                       gp120   V  gp41
HXB2  LysArgArgValValGlnArgGluLysArg AlaValGly...IleGlyAlaLeuPheLeu    520
BRU   ----------------------------------------------------------------  525
MN    ----------------------------------- Ala...-----------------------  521
SC    --------------------------------------Thr---------Met------------  520
SF2   --------------------------------------IleVal------Met------------  519
NY5
CDC4  --------------------------------------MetLeu------Met------------  530
WMJ2  --------------------------------------Thr---------Met------------  511
RF    --------------------------------------Thr---------Met------------  529
MAL   ---------------Glu--------------------Ile------Leu------Met------  522
ELI   ---------------Glu--------------------Ile------Leu------Met------  517
Z6    ---------------Glu--------------------Ile------Leu------Met------  519
Z3
Z321  ---------------Ala--------------------Ile---Met...------Phe------  520
JY1   ---------------Glu--------------------Ile------Leu------Val------  527

HXB2  GlyPheLeuGlyAlaAlaGlySerThrMetGlyAlaAlaSerMetThrLeuThrValGln       540
BRU   ----------------------------------------Arg----------------------  545
MN    ----------------------------------------Val----------------------  541
SC    ----------------------------------------Thr----------------------  540
SF2   ----------------------------------------Val---Leu----------------  539
NY5
CDC4  ----------------------------------------Thr-------Ala------------  550
WMJ2  ----------------------------------------Gly---Leu----------------  531
RF    ----------------------------------------Gly---Ile----------------  549
MAL   ----------------------------------------Leu----------------------  542
ELI   ----------------------------------------Arg---Val----------------  537
Z6    ----------------------------------------Val----------------------  539
Z3
Z321  ----------------------------------------Ile----------------------  540
JY1   ----------------------------------------Val---ValAla------Gly---  547
```

FIG. 20

```
HXB2  AlaArgGlnLeuLeuSerGlyIleValGlnGlnGlnAsnAsnLeuLeuArgAlaIleGlu    560
BRU   ------------------------------------------------------------    565
MN    ------Leu---------------------------------------------------    561
SC    ------Leu---------------------------------------------------    560
SF2   ------------------------------------------------------------    559
NY5
CDC4  ---------------------------------------------------------Lys    570
WMJ2  ---------------------------------------------------------Asp    551
RF    ------His---------------------------------------------------    569
MAL   ------------------------------------------------------------    562
ELI   ---------------Met------------------------------------------    557
Z6    ---------------Met------------------------------------------    559
Z3
Z321  ------Arg---------------------------------------------------    560
JY1   ------------------------------------------------------------    567

HXB2  AlaGlnGlnHisLeuLeuGlnLeuThrValTrpGlyIleLysGlnLeuGlnAlaArgIle    580
BRU   ------------------------------------------------------------    585
MN    ------------Met------------------------------------------Val    581
SC    ---------------------------------------------------------Val    580
SF2   ---------------------------------------------------------Val    579
NY5
CDC4  ------------------------------------------------------------    590
WMJ2  ---------------------------------------------------------Val    571
RF    ---------------------------------------------------------Val    589
MAL   ---------------------------------------------------------Val    582
ELI   ------------------------------------------------------------    577
Z6    ------------------------------------------------------------    579
Z3
Z321  ------------------Lys---------------------------------------    580
JY1   ------------Met------------------------------------------Val    587
```

FIG. 2P

```
HXB2  LeuAlaValGluArgTyrLeuLysAspGlnGlnLeuLeuGlyIleTrpGlyCysSerGly    600
BRU   ------------------------------------------------------------   605
MN    ---------------------------------------------Phe------------   601
SC    ----------------Arg-----------------------------------------   600
SF2   ----------------Arg-----------------------------------------   599
NY5
CDC4  ---------------------------------------------Phe------------   610
WMJ2  ----------------Arg-----------------------------------------   591
RF    ----------------Arg-----------------------------------------   609
MAL   ----------------Gln-------Arg------------Met----------------   602
ELI   ------------------------------------------------------------   597
Z6    ------------------------------------------------------------   599
Z3
Z321  ------------------------------------------------------------   600
JY1   -----------Ser----------------------------------------------   607

*                [     ]     [     ]
HXB2  LysLeuIleCysThrThrAlaValProTrpAsnAlaSerTrpSerAsnLysSerLeuGlu    620
BRU   ------------------------------------------------------------   625
MN    -----------------Thr-------------------------------------Asp   621
SC    -----------------Thr------------Thr----------------------Asp   620
SF2   -----------------Thr----------------------------------------   619
NY5
CDC4  ---------------------------------------------------Thr---Asp   630
WMJ2  -----------------Thr---------------------------------MN        611
RF    -----------------Thr-------------------------------------Asn   629
MAL   ---His-----------Phe------------Ser----------Arg------Asp     622
ELI   ---His-----------Asn------------Ser----------Arg------Asn     617
Z6    -----------------Thr------------Ser----------Arg------Asn     619
Z3
Z321  ---Ile-------Pro---Asn-------------Ser-----------------GlnSer  620
JY1   ---His-----------Thr------------Ser--------------------------  627
```

FIG. 2Q

```
       [               ]                              [          ]
HXB2  GlnIleTrpAsnHisThrThrTrpMetGluTrpAspArgGluIleAsnAsnTyrThrSer   640
BRU   ------------AsnMet-------------------------------------------  645
MN    Asp---------AsnMet---------Gln---Glu---------Asp------------  641
SC    Lys------GlyAsnMet------------------Glu---------Asp----------  640
SF2   Asp------AspAsnMet---------Gln---Glu---------Asp---------Asn  639
NY5
CDC4  ------------AsnMet-------------------------------Asp---------His  650
WMJ2  ---------AspAsnLeu------------------Glu---------Asp------------  631
RF    Met---------AsnMet---------Gln---Glu---------Asp---------Gly  649
MAL   Asp---------AsnMet---------Gln---GluLys------Ser---------Gly  642
ELI   Glu------GlnAsnMet------------------Glu---------Asp---------Gly  637
Z6    Asp------GlnAsnMet------------------Glu---------Asp---------Gly  639
Z3
Z321  Asp------AspLysMet------Leu---------Lys---ValSer---------Gln  640
JY1   Glu---------AsnMet------Ile------Glu---------Asp---------Gly  647

HXB2  LeuIleHisSerLeuIleGluGluSerGlnAsnGlnGlnGluLysAsnGluGlnGluLeu   660
BRU   ------------------------------------------------------------  665
MN    ------Tyr------Leu---Lys------Thr---------------------------  661
SC    ------TyrThr------------------------------------------------  660
SF2   Thr---TyrThr---Leu------------------------------------------  659
NY5
CDC4  ------TyrThr------------------------------------Gln---------  670
WMJ2  Ile---Tyr---------------------------Gly---------------------  651
RF    Ile---TyrAsn---Leu------------------------------------------  669
MAL   Ile---TyrAsn------------------Ile------------------Lys------  662
ELI   ------Tyr---------------------Thr------------------Lys------  657
Z6    ------TyrArg------------------Thr---------------------------  659
Z3
Z321  Val---TyrAsn------------------Thr---------Ile------ArgAsp---  660
JY1   Val---Tyr------------Asn------Ile---------------------Asp---  667
```

FIG. 2R

```
                                      [            ]
HXB2  LeuGluLeuAspLysTrpAlaSerLeuTrpAsnTrpPheAsnIleThrAsnTrpLeuTrp    680
BRU   ------------------------------------------------------------    685
MN    ---------------------------------------Asp------------------    681
SC    ------------------------------------------------------------    680
SF2   ---------------------------------------Ser------------------    679
NY5
CDC4  ---Gln-----------------------Thr---SerAsp------Lys----------    690
WMJ2  ---------------------------------------Asp------------------    671
RF    ------------------Asn------------------Asp------Gln---------    689
MAL   ---------------------------------------Ser---SerLys---------    682
ELI   ---------------------------------------Ser------Gln---------    677
Z6    ------------------------------------------------Gln---------    679
Z3
Z321  ---Ala------------Asn------------------Asp---Ser------------    680
JY1   ---Gln---------------------------------Ser------Lys---------    687

HXB2  TyrIleLysLeuPheIleMetIleValGlyGlyLeuValGlyLeuArgIleValPheAla    700
BRU   ---------Ile------------------------------------------------    705
MN    ---------Ile------------------------------------------------    701
SC    ---------Ile---------------------------------------------Thr    700
SF2   ---------Ile------------------------------------------------    699
NY5
CDC4  ---------Ile---------------------Ile------------------------    710
WMJ2  ---------Ile---------------------Ile---------------------Thr    691
RF    ------ArgIle------------------------------------Lys---------    709
MAL   ------ArgIle------IleVal---------------Ile-----------Ile----    702
ELI   ---------Ile------------Ile------------Ile------------------    697
Z6    ---------Ile---------------------Ile------------------------    699
Z3
Z321  ---------Ile---------------------Ile------------------------    700
JY1   ---------Ile---------------------Ile---------------------Thr    707
```

FIG. 2S

```
                                                          \/ 3' sj
HXB2  ValLeuSerIleValAsnArgValArgGlnGlyTyrSerProLeuSerPheGlnThrHis   720
BRU   ----------------------------------------------------------     725
MN    --------------------------------------------Leu------Arg       721
SC    ----------------------------------------------------Arg        720
SF2   ----------------------------------------------------Arg        719
NY5
CDC4  ----------------------------------------------------Leu        730
WMJ2  ----------------------------------------------------           711
RF    ----------------------------------------------------           729
MAL   ---------Leu--------------------------------Leu------Leu       722
ELI   ---------Leu----------------------------------------Leu        717
Z6    ---------Leu----------------------------------------Leu        719
Z3
Z321  ---------Ile----------------------------------------Leu        720
JY1   ---------Leu----------------------------------------Leu        727

<- tat cds end
HXB2  LeuProIleProArgGlyPro....AspArgProGluGlyIleGluGluGluGlyGlyGlu  739
BRU   ------Thr---------------------------------------------------   744
MN    Pro---Val---------------------------------------------------   740
SC    ------SerGln------------------------------------------------   739
SF2   ------Val------------------------Asp------------------------   738
NY5
CDC4  ------Asn------------------------------Thr------Gly---------   749
WMJ2  ------Thr---------------------------------------------------   730
RF    ------Ala------------------------------Gly------------------   748
MAL   ------Thr---------Pro---------------------------------------   742
ELI   ------Ala------------------------------Thr------------------   736
Z6    ------Ala------Glu------------------------------------------   738
Z3
Z321  ThrHisHisGln---Glu------------------Arg---------Gly---------   739
JY1   ------Ala---------------------------------------------------   746
```

FIG. 2T

```
                             [              ]
HXB2  ArgAspArgAspArgSerIleArgLeuValAsnGlySerLeuAlaLeuIleTrpAspAsp    759
BRU   ------------------------------------------------------------    764
MN    ------------Thr---Gly---------His---Phe------Ile------Val---    760
SC    ------------------Gly---------Asp---Phe------Ile------Val---    759
SF2   ------------------Val---------Asp---Phe-------------------Glu---  758
NY5
CDC4  ---Gly-------Gly---Thr---------His---Phe---------Val---------    769
WMJ2  ------------------Val---------His---Phe-------------------------   750
RF    ----------------GlyGlyAla------------Phe---Thr------------------   768
MAL   GlnGly---Gly-------------------------PheSer---------------------   762
ELI   ---Gly------------Val------Leu-------PheSer---------------------   756
Z6    ---Gly------------------------------PheSer----------------------   758
Z3
Z321  Gln-----------------------Ser---Phe---Pro---Ala-----------       759
JY1   GlnGly------------------------PheSer------Phe-------------       766

*
HXB2  LeuArgSerLeuCysLeuPheSerTyrHisArgLeuArgAspLeuLeuLeuIleValThr    779
BRU   ------------------------------------------------------------    784
MN    ------------Phe---------------His...----------------AlaAla       779
SC    +++---------------------------------------------------------    779
SF2   ------------------------------Arg-------------------AlaAla       778
NY5
CDC4  ---------------------------------------------------Ala          789
WMJ2  ---------------------------------------------------Lys          770
RF    ---TrpThr------Ser---------------------------------Val          788
MAL   ------Asn------------------------------------------Ala---       782
ELI   --------------------------------------------Ile------AlaVal     776
Z6    ------Asn------------------------------------Ile------AlaAla    778
Z3
Z321  ----------------Cys-------------------CysAla------AlaAla        779
JY1   ------Asn------------------------------------Ile------Ala---    786
```

FIG. 2U

```
HXB2   ArgIleValGluLeuLeuGlyArgArgGlyTrpGluAlaLeuLysTyrTrpTrpAsnLeu    799
BRU    ------------------------------------------------------------    804
MN     ------------------------------Val---------------------------    799
SC     ------------------------------------------------------------    799
SF2    ---Thr------Ile------His--------------------------Ser---       798
NY5
CDC4   ------------------------------Val---------------------------    809
WMJ2   ------------------------------------------------------------    790
RF     ------------------------------------------------------------    808
MAL    ---------------------------------------------Leu---------      802
ELI    ------------------------------AspIle---------Leu---------      796
Z6     ---------------------------------------------Leu---------      798
Z3
Z321   ------------The---Ile----------------Thr---------LeuGly------    799
JY1    -----------------------------------Ile------Leu---Ser---        806

← trs/art cds end  [        ]
HXB2   LeuGlnTyrTrpSerGlnGluLeuLysAsnSerAlaValSerLeuLeuAsnAlaThrAla    819
BRU    ------------------------------------------------------------    824
MN     ------------------------Ser---------------------------------    819
SC     ------------------------Arg------------------PheVal----------    819
SF2    ------------Ile---------------------------Trp---------------    818
NY5
CDC4   ---------------------------------------------Val---Val------    829
WMJ2   ------------Lys---------------------Gly-----------Ile---        810
RF     ---------------------------------------------------Thr------    828
MAL    ------------Gly---------------------Ile-----------Thr------    822
ELI    ------------------------Arg----------Ser------PheAsp---Ile---    816
Z6     ------------Arg---------Arg----------Ser----------AspThrIle---    818
Z3
Z321   ValIle------Gly----------------------IleAsn------AspThrVal---    819
JY1    -----------Thr-------------------Phe-Ile--------------------    826
```

FIG. 2V

```
                                                          *
HXB2   IleAlaValAlaGluGlyThrAspArgValIleGluValValGlnGlyAlaCysArgAla    839
BRU    ------------------------------------------------------------    844
MN     ---------------------------------------Leu---Arg---Gly------    839
SC     ---------------------------------------LeuLeu---Arg---Phe------ 839
SF2    ----------Thr-------------------------------Ala---Arg---Tyr------ 838
NY5
CDC4   -----------------------------------------------ArgIleTyr------   849
WMJ2   -----------------------------------------------ArgIle---------   830
RF     ------------------------Ile---------Ala---ArgIleLeu------        848
MAL    ------------Cys------------------IleGly---ArgPheGly------        842
ELI    ------------------------------------IleIle---Arg------------     836
Z6     ------------------------------------Ile---ArgArgThrTyr------     838
Z3
Z321   ------------AspTrp--------------------------Arg---Gly------      839
JY1    ------------------------Ile------LeuIleArgArg---Phe------        846

HXB2   IleArgHisIleProArgArgIleArgGlnGlyLeuGluArgIleLeuLeu+++           857
BRU    ------------------------------------------------------------    862
MN     ---Leu----------Thr------------------------Ala---------          857
SC     ---Leu----------Thr------------------------Ala---Gln---          857
SF2    ---Leu------His----------------------------Leu---------          856
NY5
CDC4   PheLeu-----------------------Phe------Ala---------               867
WMJ2   ---Ile-----------------------------Ala---------                  848
RF     PheLeu-----------------------------Ala---------                  866
MAL    ---Leu-----------------------Phe------Ala---------               860
ELI    ValLeuAsn--------------------------Ser---------                  854
Z6     ValLeuAsnVal---Thr-----------------Leu---------                  856
Z3
Z321   PheLeuAsn--------------------------Ala---------                  857
JY1    ValLeu------------Val--------------Ala---------                  864
```

FIG. 2W

PURIFIED GP120 COMPOSITION RETAINING NATURAL CONFORMATION

This application is a divisional of application Ser. No. 08/240,073, filed May 9, 1994 which is a continuation of application Ser. No. 08/109,002, filed Aug. 16, 1993, which is a continuation of application Ser. No. 07/684,963, filed Aug. 20, 1991, which is a continuation-in-part of Ser. No. 07/490,858, filed Mar. 9, 1990.

INTRODUCTION

1. Technical Field

The present invention is directed generally to the field of protein purification and more particularly to the purification of HIV-1-derived antigens useful in the production of vaccines,

2. Background

Attempts at making vaccines against HIV-1 have met with limited success, as measured by the criterion of achieving in animals an immune response similar or equivalent to that of humans that are sero positive to HIV-1. The major goal, not previously attained, has been the generation of antibodies that are virus neutralizing in vitro at titers reaching both the level and complexity (i.e., ability to neutralize more than one isolate) seen in human sera from infected individuals. All of the neutralizing antibodies in humans have mapped to the envelope protein, gp160, or one of its component parts (gp120 or gp41), and thus most vaccine efforts have concentrated on the development of envelope-protein-related antigens.

Five types of such antigens have been developed: (1) purified gp120 derived from HIV-infected tissue culture cells (referred herein as "viral-derived gp120"); (2) gp120 made in cells infected with recombinant viruses, such as vaccinia or baculovirus ("live-virus-vector-derived gp120 and gp160"); (3) recombinant gp120 made in mammalian cells ("recombinant mammalian gp120," sometimes referred to incorrectly as recombinant native gp120); (4) recombinant denatured polypeptides that represent all or various portions of gp120 and gp41 ("recombinant denatured antigens"); and (5) peptides that represent small segments of gp120 and gp41 ("peptides").

Immunogenicity experiments have been completed with all of these types of antigens, with fairly uniform results. In general, the antigens are highly immunogenic as adjuvanted in a variety of species. They have generated antibodies capable of neutralizing the homologous isolate of HIV-1, but they poorly or not at all neutralize non-homologous isolates. The levels of neutralization also have not (in general) reached the level of neutralizing titer found in infected humans.

For example, fully glycosylated gp120 natural purified from virus or produced by genetically engineered mammalian cells, non-glycosylated gp120 produced in yeast, and a fragment of gp120 produced in E. coli can all elicit HIV-1 neutralizing antibodies in experimental animals. For the most part, the responses of animals immunized with virion or recombinant gp120 antigens are effective in neutralizing only the virus isolate from which the gp120 antigen originated. One exception is the work of Berman et al. (reference 1 below) showing that purified recombinant HIV-1 gp120 secreted by genetically engineered Chinese hamster ovary cells elicited group-specific neutralizing antibodies in chimpanzees.

Another factor that has been particularly difficult to overcome when preparing HIV-1 vaccines is sequence diversity. HIV-1 and HIV-2 are characterized by having a very high level of sequence diversity that is most pronounced in the gp120 portion of the envelope. This sequence diversity is clustered in regions known as hypervariable regions. Many groups have proposed using a vaccine cocktail, comprising antigenic substances derived from a variety of HIV isolates, to provide protection against a broad range infective sources.

Accordingly, there remains a need for an antigenic substance having immunological and other protein/protein binding properties of gp120 as it is presented on an HIV-1 virus particle. In particular, antigenic substances capable of inducing neutralizing antibodies, preferably using a single source material that induces neutralizing antibodies against a variety of field isolates, are highly desirable.

Relevant Literature

The following publications are all directed to the five types of vaccine candidates described above:

(1) Berman et al., "Human Immunodeficiency Virus Type I Challenge of Chimpanzees Immunized with Recombinant Envelope Glycoprotein gp120," Proc. Natl. Acad. Sci. USA (1988) 85: 5200–5204;

(2) Berman et al., "Expression and Immunogenicity of the Extracellular Domain of the Human Immunodeficiency Virus Type I Envelope Glycoprotein, gp160," Journal of Virology (1989) 63: 3489–3498;

(3) Nara et al., "Purified Envelope Glycoproteins from Human Immunodeficiency Virus Type I Variance Induced Individual, Type-Specific Neutralizing Antibodies," Journal of Virology (1988) 62: 2622–2628;

(4) Arthur et al, "Serological Responses in Chimpanzees Inoculated with Human Immunodeficiency Virus Glycoprotein (gp120) Subunit Vaccine," Proc. Natl. Acad. Sci. USA (1987) 84: 8583–8587;

(5) Evans et al., "An Engineered Polio Virus Chimaera Elicits Broadly Reactive HIV-1 Neutralizing Antibodies," Nature (1989) 33.9: 385–388;

(6) Barrett et al., "Large-Scale Production and Purification of a Vaccinia Recombinant-Derived HIV-1 gp160 and Analysis of its Immunogenicity," AIDS Research and Human Retroviruses (1989)5: 159–171;

(7) Earl et al., "Isolate- and Group-Specific Immune Response to the Envelope Protein of Human Immunodeficiency Virus Induced by a live Recombinant Vaccinia Virus in Macaques," AIDS Research and Human Retroviruses (1989) 5: 23–32;

(8) Putney et al., "HTLV-III/LAV-Neutralizing Antibodies to an E. coli-produced Fragment of the Virus Envelope," Science (1986) 234: 1392–1395;

(9) Steimer et al., "Genetically Engineered Human Immunodeficiency Envelope Glycoprotein gp120 Produced in Yeast is the Target of Neutralizing Antibodies," Vaccines 87 (1987) 236–241;

(10) Steimer et al., "Recombinant env and gag Polypeptides in Characterizing HIV-1-Neutralizing Antibodies," Vaccines 88 (1988) 347–355;

(11) Ho et al., "Human Immunodeficiency Virus Neutralizing Antibodies Recognize Several Conserved Domains on the Envelope Glycoproteins," Journal of Virology (1987) 61: 2024–2028; and

(12) Palker et al., "Type-Specific Neutralization of the Human Immunodeficiency Virus with Antibodies to env-Encoded Synthetic Peptides," Proc. Natl. Acad. Sci. USA (1988) 85: 1932–1936.

SUMMARY OF THE INVENTION

It is an object of the present invention to provide a method for purifying HIV gp120 so as to provide a glycopeptide having protein/protein binding properties substantially identical to natural viral HIV gp120.

It is also an object of the present invention to provide a composition comprising purified, full-length (non-fusion if recombinant) HIV gp120 glycoprotein the majority of the molecules of which have protein/protein-interaction properties substantially identical to gp120 as presented on an HIV virus.

It is a further object of this invention to provide a method for stimulating the formation of antibodies capable of neutralizing infection by multiple HIV viral isolates.

It is yet another object of the present invention to provide a vaccine composition, which when, administered to a mammalian subject, reduces the susceptibility of that subject to infection by HIV viruses from a variety of sources.

It is a further object of the present invention to provide a vaccine composition which, when administered to a mammalian subject infected with HIV-1, has a therapeutic effect.

These and other objects of the invention as will hereinafter become more readily apparent have been achieved by providing in one embodiment a method for purifying gp120 from a medium which contains a full-length, non-fusion, glycosylated gp120 protein, which comprises sequentially fractionating the gp-120-containing medium using (1) ion exchange chromatography, (2) hydrophobic-interaction chromatography, and (3) size-exclusion filtration (size exclusion chromatography or gel filtration chromatography), collecting at each step a fraction that exhibits specific binding affinity for CD4 peptide. By selecting purification steps from these techniques and avoiding affinity chromatography and reverse-phase HPLC, it is possible to obtain a purified gp120 molecule that has never been denatured or subjected to harsh solvent conditions, such as would occur in an affinity chromatography column using antibodies or other binding molecules having high specific affinity for gp120. The gp120 of the present invention, referred to as conformation-retained gp120, retains binding properties to the CD4 receptor that much more closely resemble natural gp120 as presented by viral particles than was previously available. Thus, another embodiment of the invention is a composition comprising gp120 wherein the majority of the gp120 is conformation-retained gp120. Additional embodiments of the invention include the use of such improved gp120 compositions in immunological methods, such as immunoassays for anti-HIV antibodies, in the production of anti-HIV antiserum, and in vaccines.

DESCRIPTION OF THE DRAWINGS

The invention will be better understood by reference to the following description of specific embodiments in combination with the drawings that are part of the present specification, wherein:

FIGS. 2A–D are tables of aligned amino acid sequences for various HIV-1 isolates with the constant (C) and variable (D) domains indicated. Potential N-linked glycosylation sites for the HXB2 sequence only are indicated by []; cysteine residues have * above them in this figure. This sequence data was published in Human Retroviruses and AIDS 1988, A Compilation and Analysis of Nucleic Acid and Amino Acid Sequences, edited by Gerald Myers et al., published by the Theoretical Biology and Biophysics Group, T-10, Mail Stop K710, Los Alamos National Laboratories, Los Alamos, N. Mex., 87545. There is also a 1989 version edited and published by the same source.

DESCRIPTION OF THE SPECIFIC EMBODIMENTS

General Principles of Purification

Figure 1:
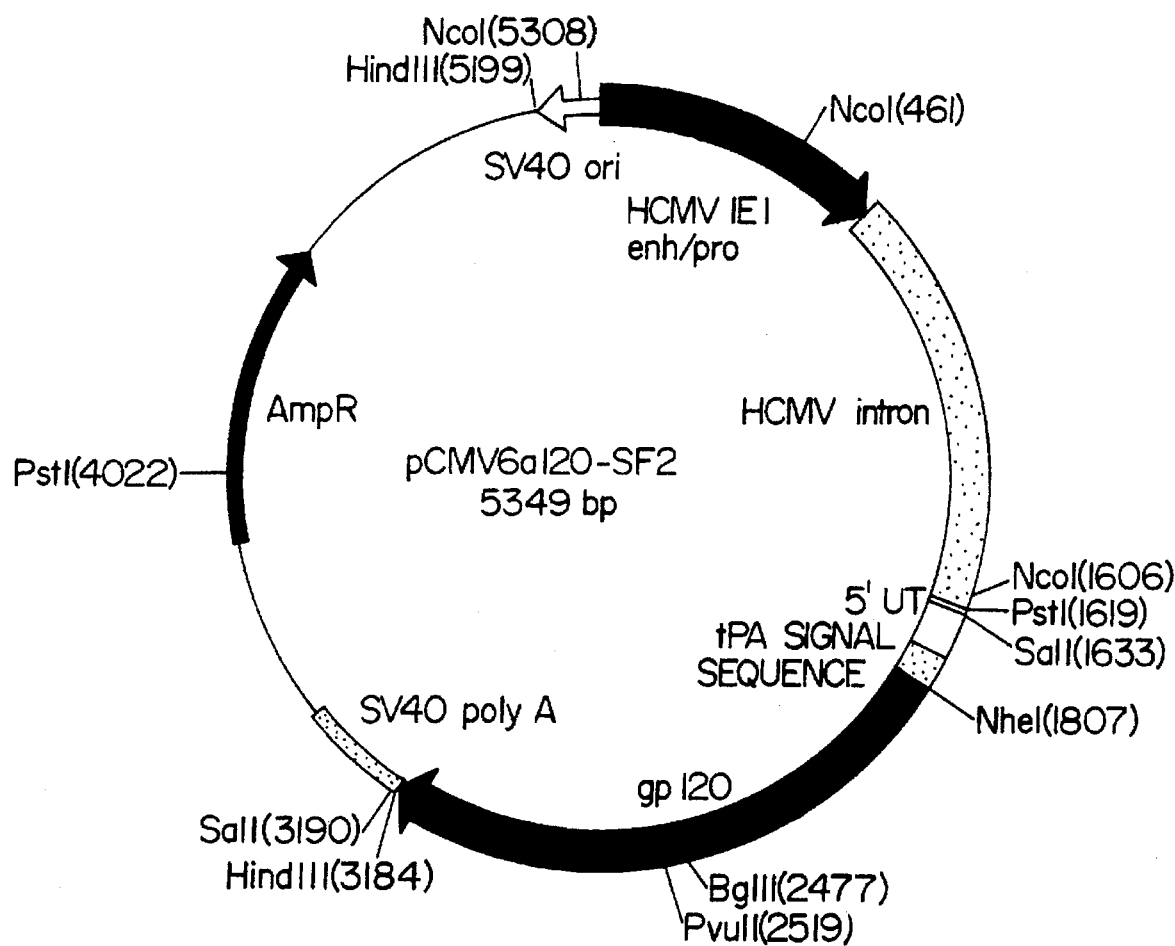
FIG. 1 is a schematic diagram of an exemplary expression plasmid for the production of recombinant HIV-1 gp120 (rgp120).

The present invention arose in part from investigations in the laboratory of the present inventors which demonstrated that eliminating affinity chromatography from previous purification techniques produced a gp120 glycopeptide composition with better CD4 binding properties. Affinity purification was previously thought to be essential in the purification of gp120 for use in vaccines where high degrees of purity are required.

Affinity chromatography and other types of affinity separation techniques rely on the strong and specific binding interaction between an antibody and a protein (or between a lectin and a glycoprotein) in order to separate the protein from other molecules present in the medium in which the protein is found. Appropriate techniques, such as changing the ionic strength or pH of the elution medium, are then used to dissociate the antibody from the protein so that the purified protein can be obtained after other contaminating proteins have been washed off the column or other support material to which the antibody is attached. Affinity chromatography has been in use for more than twenty years in the field of biochemistry, but its use increased rapidly with the advent of monoclonal antibodies of high specificity in the early 1970s. For a review of the technology, see Freifelder, *Physical Biochemistry: Applications to Biochemistry and Molecular Biology*, 2nd ed., W. H. Freeman & Co., San Francisco, 1982, pp. 257–262.

However, the present inventors have discovered that an apparent change in confirmation takes place in this 2-step binding/removal process when affinity chromatography is used to purify the gp120 molecule so that the resulting gp120 protein, although purified, does not present the same epitopes as the viral gp120 molecule for inducing antibody formation or for undergoing protein/protein binding interactions, such as binding with the CD4 molecule. Thus, affinity-purified gp120 does not resemble gp120 as presented by a virus particle to a sufficient extent to allow such purified proteins to be used in the induction of neutralizing antibodies to the extent that would be desired in, for example, an efficient vaccine.

It will be recognized that discussion of a particular composition of gp120 as having a specified property, such as ability or inability to bind CD4, relates to the composition as a whole and is not intended to represent the properties of each and every gp120 molecule in the composition on the molecular level. For example, a composition of gp120 as purified using published techniques may refer to a composition of gp120 as having, for example, 10% of the binding capacity for CD4 of natured gp120 as presented on an HIV-1 virus. This could mean that binding affinity of each and every molecule has been reduced by 90%, but it is more likely that some molecules retain their original conformation and binding affinity while a majority of the molecules have been modified in some way (e.g., have a changed conformation) so that they have lost all or pad of their binding affinity. Accordingly, a variety of gp120 molecules having different properties are likely to be present in any gp120 composition, and the effectiveness of a purification technique in retaining natural binding properties is best measured by the binding properties of the composition as a whole.

The present inventors have discovered that it is possible to purify HIV gp120 so as to provide a glycopeptide composition having protein/protein binding properties (particularly CD4 binding) substantially identical to natural viral HIV gp120. In a composition of the invention, 50% or more, preferably 80% or more, and most preferably 90% or more of the molecules are in a conformation that allows binding to a CD4 molecule, as opposed to about 10% or less of gp120 molecules even in unpurified compositions produced by some published techniques.

The process of the invention begins with a gp120 source, such as a cell medium into which a gp120 molecule has been secreted or a cell or viral lysate. The present invention is particularly useful for providing in pure form with its natural retained conformation, and for purifying, a full-length, non-fusion, glycosylated recombinant gp120 protein that has been secreted into the cell medium. Here a "recombinant gp120 protein" refers to a protein produced by a non-HIV-infected cell, whether that cell contains the appropriate gp120 gene as a result of transfection, chromosomal insertion, retention of a plasmid, or other means of expressing the protein. However, gp120 from viral sources can also be used. Preparation of the original crude composition containing gp120 is not a part of the broader aspects of the present invention, as gp120 has previously been prepared from both recombinant and viral sources. Discussion of gp120 sources is therefore deferred until a later section of the specification in which preferred embodiments of the present invention are discussed.

It is necessary to replace affinity chromatography (and reverse-phase HPLC or other techniques that use organic solvents) with a separation technique that does not disrupt the desired conformation of the gp120 molecule. Surprisingly, it has been discovered that hydrophobic-interaction chromatography (HIC) provides the desired purification when used in combination with ion exchange chromatography and gel filtration chromatography. This finding was unexpected since gp120 is a glycoprotein with 22 known glycosylation sites and therefore is expected to be highly hydrophilic (rather than hydrophobic). It has been discovered that gp120 has at least one region of sufficient hydrophobicity to allow good separation from contaminants using an HIC purification step. For example, nearly 10-fold purification was achieved on a phenyl HIC column. FIG. 3A shows that gp120 was the last fraction to elute from this column. Although hydrophobic regions were previously known to exist in the amino acid sequence (from hydrophobicity plots), it was not known or suggested that sufficient hydrophobicity was retained after glycosylation to allow separation of gp120 from other proteins using HIC.

Each of the steps of the purification process is discussed in detail below. In general, the purification process comprises concentrating the cell medium or other gp120 source to increase the concentration of gp120, typically by removing water and other small molecules; fractionating the concentrated cell medium using an ion exchange material and collecting a fraction that exhibits specific binding affinity for the CD4 peptide; fractionating this first fraction using hydrophobic interaction chromatography (preferably using two HIC steps) so as to provide a second fraction exhibiting proper CD4 binding affinity; and fractionating the second fraction by size exclusion filtration or chromatography to provide the desired purified protein. This discussion will generally refer to the gp120 source as a cell culture medium, as this is the most common source. However, other sources of gp120 can be used interchangeably with a cell culture medium.

The concentrating step is a conventional first step used in purification of many proteins from a variety of sources, namely removing water and other small molecules from the cell medium so that subsequent purification steps can be carried out on a relatively small volume of material. Therefore any of a variety of size fractionating techniques can be used. Dialysis and ultrafiltration are preferred techniques. The initial concentrating step can merely remove water and other small molecules, such as those having molecular weights of 1,000 or less, or techniques that remove some or substantially all molecules smaller in molecular weight than the gp120 molecule can be used. For example, ultrafiltration can be carried out using membranes having a variety of cut off values, such as molecular weights of 10,000, 20,000, 30,000, 50,000, or 100,000. Molecular weight cut offs in the range of 10,000 to 50,000 are preferred, preferably about 30,000.

After concentration of the cell culture medium to eliminate small molecules, the concentrated cell medium containing molecules larger than the cut off size is fractionated using an ion exchange material. Peptides from different sources may behave differently on ion exchange fractionation because of different charges. For example, gp120 obtained using genetic material originally isolated from the HIV-SF2 isolate is not retained on a DEAE Sephadex column at a pH of 8 in 0.1M NaCl, while gp120 from the isolate HIV-HTLV-IIIB binds to the column under the same conditions and can be eluted with a salt gradient of from 0.1 to 0.5M NaCl. Whether or not the particular gp120 molecule sticks to the column is immaterial, however, since the ion exchange process, including elution, does not appear to adversely effect immunological or other protein/protein binding properties.

The ion exchange step can be a single step or can be divided into two or more steps. Treatment with a anion exchange resin is preferred for at least one substep (or as the only ion exchange step). The anion exchangers typically comprise aromatic or aliphatic amino groups and include DEAE-SEPHADEX, which is diethylaminoethyl-substituted dextran, or AG-3, which has a tertiary amino substituent on an epoxy amine resin. As an alternative to these weakly basic materials, quaternary ammonium ions and other exchange materials exhibiting full positive charges can be used, such as Q-SEPHAROSE-HP, a product of Pharmacia that has a quaternary ammonium ion bound to a sepharose column. For the anionic exchange step, a buffer with a pH in the 7–9 range is typically used, preferably about pH 8. A typical example buffer is Tris, 0.02M. Ionic strengths are normally in the range of from about 0.05 to 0.2M (expressed as NaCl), preferably around 0.1M. Other conditions that should be controlled include temperature (e.g., about 0° to 25° C.), total conductivity of material applied to the column (e.g., about 15 mS-cm), and the ratio of protein load to resin volume (e.g., about 15 to 20 g/L). These values are preferred values for a DEAE-SEPHADEX column and can be varied for the other column materials in accordance with manufacturer's suggestions.

Alternatively, cell culture media can be purified by cationic exchange chromatography using a weakly or strongly acidic exchange group, such as a carboxylic acid or sulfonic acid group, respectively, although such separations are less preferred than use of anion exchangers. A typical strongly acidic system, for example, can use a sulfopropyl ion exchange resin such as SP-SEPHADEX. A gp120-containing cell medium is typically added and eluted at a pH in the range of from about 6 to about 8, preferably a pH of about 7. Other conditions are similar to those used for anion exchange columns.

Fractions that contain the desired gp120 molecules can be identified by any of the numerous known techniques for identifying gp120, such as recognition by antibodies, binding by CD4 peptide, or SDS gel electrophoresis. Fractions containing the gp120 molecules can be identified by carrying out analyses on aliquots taken from each fraction. After a fractionation pattern is established, the ion exchange procedures are sufficiently repeatable so that fractions can be collected without testing. CD4 binding was checked for each new step of the present invention as it was incorporated into the process, and CD4 binding can be used to verify whether any modification from the specific, preferred conditions described herein (such as changing column support materials, temperatures, buffers, etc.) provide a gp120 composition within the scope of the invention. Additional details on measuring binding between CD4 and gp120 are set forth in a later section of this specification.

The most definitive test for gp120 is binding of the CD4 peptide. Binding to the CD4 peptide is typically verified by radioimmune precipitation or gel filtration HPLC as described in the examples that follow. Any fractions containing the gp120 material can be purified individually or after combining the fractions to provide pooled material for use in a later purification step.

Although reference is generally made herein to the ability of a gp120 molecule in a particular fraction to bind to the CD4 peptide, use of such language does not mean that an actual binding assay for CD4 peptide is carried out at each step. Rather, the language is used to indicate, whether for this or a different step, that conditions are maintained so that ability of gp120 to bind the CD4 peptide is not lost at any step of the separation technique.

The next purification step involves hydrophobic-interaction chromatography, in which passage of molecules through a column is retarded by hydrophobic interactions between the column support material (or a substance bound to the support material) and the molecules being fractionated. Typical of such fractionating processes are high performance liquid chromatography processes using a hydrophobic column. A typical column is an ether-HIC or phenyl-HIC column. An ether-HIC column contains aliphatic groups linked to a column support material by an ether linkage, while a phenyl-HIC column contains phenyl groups linked to the support material. As is understood by those of ordinary skill in the HIC techniques, addition of sample to the column and elution are carried out using solutions having sufficient ionic strength (which may for some molecules be zero) to cause the material being separated to "stick" to the surfaces of the resin used in the column. Lowering the ionic strength of the eluent (i.e., decreasing the concentration of salts in the eluent) reduces the tendency of hydrophobic materials to be retained by the column.

In a typical gp120 purification, fractions obtained by ion exchange chromatography are brought to 35–45%, preferably about 40%, saturation in ammonium sulfate, and any insoluble material is removed by centrifugation before the supernatant is applied to the HIC column. The treatment of the ion-exchange-chromatography fraction with, e.g., 40% saturated ammonium sulfate is useful for precipitating some contaminating proteins at this point in the process, although it is not required. The gp120 molecule does not itself precipitate in 40% saturated ammonium sulfate for all strains and mutational variations of isolates tested to date. Should gp120 from other isolates precipitate at 40% ammonium sulfate, a concentration can be selected which is below that required to precipitate gp120 but which is sufficiently high to provide an ionic strength that causes gp120 to bind to the HIC column. Other salts can be used in place of ammonium sulfate if desired. The salt concentrations discussed in this paragraph are exemplary, and other salts and salt concentrations can be used by varying flow rates, temperatures, and elution times as is known in the art. Ammonium sulfate is preferred because it generally stabilizes protein structure when present at high concentrations.

A variety of hydrophobic interaction chromatography resins can be used, and the present invention is not limited to a particular resin. Example of typical HIC columns include butyl (butyl Foyo Pearl, Toyo Soda) octyl (octyl Sepharose, Pharmacia) and Phenyl (Phenyl Sepharose, Pharmacia) As with ion exchange chromatography, separation based on hydrophobic interactions does not appear to adversely affect the confirmation of the protein.

Conditions under which these column are used vary with the specific columns as is known in the art. Typical conditions include a pH of from about 5 to about 7 (e.g., 0.02M sodium acetate, pH 5.0); an ionic strength of from about 0.05 to 2.0M (expressed as NaCl), preferably about 0.1M; and elution using a gradient from 40% ammonium sulfate (or a different initial concentration as described above) decreasing to 0% ammonium sulfate.

It is possible to use a single HIC step, but at least two HIC substeps are preferred, preferably using different HIC supports (e.g., separation on a phenyl-HIC column followed by separation on an ether-HIC column). However, two separations on the same column (e.g., a phenyl-HIC column) can be used. Conditions can be adjusted using known techniques to provide for separation of peaks of protein having the desired activity from other protein-containing peaks also present in the fraction purified by ion exchange chromatography. As before, fractions containing the desired activity are collected and separated from fractions not containing such activity.

Fractions containing the desired activity as obtained from hydrophobic interaction chromatography are subjected to gel filtration (also known as gel permeation chromatography, including gel filtration HPLC techniques). If purity is sufficient after HIC, the eluent from the last HIC column can be applied directly to the gel filtration column. Purity is measured by gel electrophoresis and Coumassie Blue staining and should be at least 5%, preferably at least 50%(by weight of proteins present). However, if the desired level of purity is not attained at this stage, the process of the invention can still be carried out by subjecting the HIC eluent to ion exchange chromatography prior to gel filtration. Lower purity is sometimes seen at this stage if an inefficient expression system is used so that the initial cell medium contains a relatively small amount of gp120 compared to other proteins. HPLC ion exchange chromatography using a support material with pendant quaternary ammonium ions is particularly preferred if ion exchange or medium pressure chromatography with a high-efficiency anion exchange resin such as Pharmacia's Q Sepharose High Performance is necessary at this stage.

At this point in the purification process (i.e., after HIC and, if necessary, the second ion exchange step), the impurities being removed are mostly low-molecular-weight impurities. Again, the specific materials and conditions used are not particularly restricted. Dextran, polyacrylamide, or agarose gels can all be used. Molecular weight fractionation ranges of from 1 OK to 500K, preferably from 50K to 200K, are typically selected. A particularly preferred column for use with HPLC is SUPERDEX 200 (Pharmacia). Conditions for such use are typically 0.1M sodium phosphate, pH 6.7. Gel exclusion chromatography does not appear to adversely affect presentation of the epitopes necessary for inducing formation of neutralizing antibodies.

A protein G affinity purification can be conducted at any stage of the process, for example, after the ion exchange chromatography and before the hydrophobic-interaction chromatography to reduce or eliminate the IgG contamination, as is known in the art. Suitable methods of conducting protein G affinity purification are known in the art and include the use of affinity columns, such as Protein G Sepharose Fast Flow, Pharmacia, and the like. By way of non-limiting example, use of a 0.1M sodium phosphate buffer at pH 7 can be used, although any conventional buffer can be used.

In all of the purification steps discussed above, conditions should be maintained so as to minimize denaturation, including during collection and handling of fractions produced by the separation steps. The pH of all solutions should therefore be in the range of from about 4 to about 9, preferably from 5 to 8. Ionic strengths should be from 0.02 to 0.5M (NaCl equivalents), preferably from 0.05 to 0.3M, except for ammonium sulfate, which can be higher as stated earlier. Temperatures should be from 0° to 25° C., preferably 2° to 80° C. Detergents and organic solvents should be avoided completely. Fractions obtained by any of the steps indicated above can be concentrated by ultrafiltration or other concentration techniques to remove solvent and other small molecules, if desired. Such ultrafiltration is generally not required unless the fractionating process has diluted the fractions containing gp120, such as might occur when the gp120 peak is spread out over several fractions.

In summary, the purification procedure described above was arrived at by testing after each new step to assure that CD4 binding was undiminished. Steps which might expose the protein to denaturing conditions, such as reverse phase and immunoaffinity chromatography, were avoided. Much of the purification was achieved by exploiting the strong binding of gp120 to two different hydrophobic resins in the presence of ammonium sulfate. Additionally the purified protein bound to Superose®12, nominally a gel filtration resin, in a hydrophobic mode at neutral pH in 0.1M NaCl. This behavior was somewhat surprising in view of the hydrophilic character of carbohydrate and the fact that gp120 is more than 50% carbohydrate by weight.

The production procedure has been carded out repeatedly at the 40 L scale (starting with 40 L of cell culture supernatant), as described here. The procedure has also been used at smaller and larger scales with appropriately sized columns, ranging from 0.4 L to at least 200 L cell culture supernatant. The yield and purity of the product were nearly constant over this range of scale. Recently the cellular production has been performed in continuous suspension cultures. This modification facilitates large scale production of gp120. No significant differences in the behavior of the product have been detected from one lot to another using roller bottle or continuous culture supernatants as the starting material.

A detailed description of an actual purification process is given in the examples that follow. Although the present invention is not limited to that particular example, the example provides additional guidance by indicating specific parameters for a complete separation that comes within the scope of the present invention.

Characteristics of gp120 Produced by the Purification Process

The gp120 glycoprotein produced by the process of the present invention is pure as judged by SDS gel electrophoresis with Coomassie Blue staining and retains full activity in CD4 binding assays. Purity levels of approximately 95% are estimated. Here purity refers to absence of other proteins, since pure gp120 is a heterogeneous composition because of the differences in carbohydrate content of different gp120 molecules. The product of the purification process of the present invention appears to be indistinguishable from gp120 natural conformation as obtained from viral sources. Specific examples of assays that can be used to determine if purified gp120 has the conformation of the material obtained in the present invention are set forth in the examples that follow. Generally, these tests include CD4 binding, gel filtration HPLC (under both oxidizing and reducing conditions), and reaction with gp120-specific antisera.

Other investigators have reported that recombinant gp120 purified by a variety of techniques other than as specified herein exhibit reduced binding affinity for the CD4 receptor. Although the reason for this reduction in binding affinity is not known with certainty, it is believed to represent a change in conformation of the molecule during purification. For example, one purification scheme initially tried for gp120 by the present inventors used affinity chromatography and reverse phase HPLC. The material purified by that procedure was approximately 80% pure and exhibited the expected level of reactivity in an ELISA assay using a monoclonal antibody specific for gp120. However, the binding activity measured in vitro to the CD4 receptor was depressed approximately 10 fold. The present as item provides gp120 that is of as high or of higher purity than previously gp120 available while retaining full CD4 binding activity. Furthermore, the purification technique provides a reasonable yield of product and is suitable for large-scale production (in the range of several hundreds of milligrams or more) of gp120. Neither affinity chromatography or reverse-phase HPLC is required, thereby eliminating conformational changes associated with these purification techniques (caused by high ionic strengths and contact with organic solvents). Full activity has been observed in ELISA and CD4 receptor binding assays. The purified material, designated herein as "conformation-retained gp120 natural conformation," appears to be indistinguishable from gp120 as presented on a virus particle.

For example, the conformation-retained recombinant gp120 desired from HIV-SF2 was indistinguishable from viral HIV-SF2 gp120. The proteins had very similar mobilities on SDS gels. They displayed equivalent immunoreactivities in immune precipitations, western blots, and solid phase capture assays with all sera assayed.

The purified protein exhibited a molecular weight of 120K in reduced or non-reduced SDS gels; thus the polypeptide chain is intact. Gel filtration HPLC in a nondenaturing buffer at neutral pH yielded a molecular weight estimate of 130K showing that the purified protein has little tendency to aggregate under these conditions. The protein had a surprising hydrophobic character as evidenced by its behavior on several columns.

The binding of recombinant gp120 to CD4 was studied directly in a gel filtration HPLC assay. Like the viral gp120, rgp120 bound to CD4 with high affinity and 1:1 stoichiometry. At least 90% of the purified gp120 molecules were able to bind to CD4 as measured by this assay. Finally, the purified protein has a $K_d$ for CD4 of H6.9 nM. This value is in the range of affinities measured for the binding of viral gp120 and other purified preparations to the CD4 receptor (see, Smith et al., *Science* (1987) 238: 1704 and Lasky et al., *Cell* (1987) 50: 975).

Sources of gp120 for Purification

The broad aspects of the present invention do not include the step of preparing the source medium containing the gp120 molecule. Preparation of gp120 by recombinant techniques is described elsewhere, such as the publications cited previously in the Background section of this specification and the publications cited therein. The techniques of the present invention have been applied by the present inventors to gp120-conditioned media from a variety of cell lines containing genetic material from different HIV isolates that produce different gp120 molecules. Gp120 from non-recombinant sources can also be used (e.g., virus-infected cell lines). Specific sources of gp120 are identified in the examples that follow and a general discussion of cell culture for expression of gp120 follows, but the present invention is not limited to such sources.

SF2-gp120 served as the model for developing the present purification process. Several other cloned gp120 genes are available for other isolates of HIV-1 as well as several altered forms created by in vitro mutagenesis of gp120 genes. For example, full sequences of amino acids coded by cloned genes from 15 different HIV-1 isolates (SF2, HXB2, BRU, MN, SC, NY5, CDC4, WMJ2, RF, MAL, ELI, Z96, Z3, Z321, and JY1) are reported in Myers, et al., *Human Retroviruses and Aids*, 1990 (1990), Los Alamos, N. Mex.: Los Alamos National Laboratory, the entirety of which is incorporated herein by reference. Seven sequences (six of which are different from those shown in 90/02568) are shown in Modrow et al., *J. Virol.* (1987) 61; 570–578. Srinivasan et al., *Gener* (1987) 52: 71–82, reports an additional HIV-1 isolate sequence isolated in Zaire. Both of these publications are also incorporated by reference. The inventors' experience to date has shown that the methods described here can be used for gp120 proteins from other isolates as well as mutant forms of the gene, even though these proteins may differ considerably from SF2-gp120 in sequence and amino acid composition.

In addition to recombinant sources, natural viral sources of gp120 can be used. Cell lines harboring HIV are available from the American Type Culture Collection, Rockville, Md., USA (ATCC CRL 8543). This cell line is referenced in U.S. Pat. No. 4,520,113. Other vital isolates are described in Tersmette et al., *J. Virol.* (1988)62:2026–2032 and Popovic et al., *Science* (1984) 224: 497–500.

Recombinant sources are preferred both for ease of production and to avoid danger of infection by active HIV-1 virus. Full-length recombinant gp120 can be prepared using any of a number of known expression systems. All such systems will contain instructions encoding isolate all of the amino acids of mature gp120 (e.g., amino acids 30 or 31 to 509 of the env gene in the SF2).

HIV gp120 nucleic acid sequences may be obtained by recombinant DNA methods, such as by screening reverse transcripts of mRNA, or by screening genomic libraries from any cell. The DNA may also be obtained by synthesizing the DNA from published sequences using commonly available techniques and DNA synthesizing apparatus. Synthesis may be advantageous because unique restriction sites may be introduced at the time of preparing the DNA, thereby facilitating the use of the gene in vectors containing restriction sites not otherwise present in the native source. Furthermore, any desired site modification in the DNA may be introduced by synthesis, without the need to further modify the DNA by mutagenesis.

In general, DNA encoding the HIV gp120 polypeptide from new stains can be obtained by constructing a cDNA library from mRNA obtained from field or laboratory isolates and (1) screening with labeled DNA probes encoding portions of the envelope protein in order to detect clones in the cDNA library that contain homologous sequences or (2) amplifying the cDNA using polymerase chain reaction (PCR) and subcloning and screening with labeled DNA probes. Clones are then analyzed by restriction enzyme analysis and nucleic acid sequencing so as to identify full-length clones and, if full-length clones are not present in the library, recovering appropriate fragments from the various clones and ligating them at restriction sites common to the clones to assemble a clone encoding a full-length molecule. DNA probes can be prepared from the genetic material set forth in the accompanying examples. Any sequences missing from the 5' end of the HIV gp120 cDNA may be obtained by the 3' extension of the synthetic oligonucleotides complementary to HIV gp120 sequences using mRNA as a template (so-called primer extension), or homologous sequences may be supplied from known cDNAs.

Producing rgp120 for purification by the process of the present invention will employ, unless otherwise indicated, conventional molecular biology, microbiology, and recombinant DNA techniques within the skill of the art. Such techniques are explained fully in the literature. See e.g., Maniatis, Fritsch & Sambrook, "Molecular Cloning: A Laboratory Manual" 2nd Ed. (1989); "DNA Cloning: A Practical Approach," Volumes I and II (D.N. Glover ed. 1985); "Oligonucleotide Synthesis" (M. J. Gait ed. 1984); "Nucleic Acid Hybridization" (B. D. Hames & S. J. Higgins eds. 1985); "Transcription And Translation" (B. D. Hames & S. J. Higgins eds. 1984); "Animal Cell Culture" (R. I. Freshney ed. 1986); "Immobilized Cells And Enzymes" (IRL Press, 1986); B. Perbal, "A Practical Guide To Molecular Cloning" (1984).

In describing genetic material used to prepare recombinant gp120 for purification by the process of the present invention, the following terminology will be used in accordance with the definitions set out below.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, and/or cytosine) in either its single stranded form, or in double-stranded helix. This term refers only to the primary and secondary structure of the molecule and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic e.g., mammalian) DNA, viral DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded (inclusively) at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eucaryotic promoters will often, but not always, contain "TATA" boxes and "CAT" boxes.

A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes. For instance, alpha-factor, a native yeast protein, is secreted from yeast, and its signal sequence can be attached to heterologous proteins to be secreted into the media (See U.S. Pat. No. 4,546,082, EPO O 116 201, publication date 12 Jan. 1983. Further, the alpha-factor and its analogs have been found to secrete heterologous proteins from a variety of yeast, such as Saccharomyces and Kluyveromyces, (EPO 88312306.9 filed 23 Dec. 1988; EPO O 0 324 274 publication, and EPO Pub. No. 0 301 669, publication date 1 Feb. 1989). An example for use in mammalian cells is the tPA signal used for expressing factor VIIIc light chain.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, for example, the transforming DNA may be maintained on an episomal element such as a plasmid or viral vector. BPV transformed cells are stable and remain episomal. With respect to eucaryotic cells, a stably transformed cell is one in which the transforming DNA has become integrated into a chromosome so that it is inherited by daughter cells through chromosome replication. This stability is demonstrated by the ability of the eucaryotic cell to establish cell lines or clones comprised of a population of daughter cells containing the transforming DNA. A "clone" is a population of cells derived from a single cell or common ancestor by mitosis.

A "cell line" is a clone of a primary cell that is capable of stable growth in vitro for many generations.

Two DNA sequences are "substantially homologous" when at least about 85% (preferably at least about 90%, and most preferably at least about 95%) of the nucleotides match over the defined length of the DNA sequences. Sequences that are substantially homologous can be identified in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A composition comprising "A" (where "A" is a single protein, DNA molecule, vector, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species (with respect to the polypeptide portion of a glycoprotein, such as gp120) having the activity or characteristic of the species of interest.

An "antibody" is any immunoglobulin, including antibodies and fragments thereof, that binds a specific epitope. The term encompasses, inter alia, polyclonal, monoclonal, and chimeric antibodies. For more about chimeric antibodies, see U.S. Pat. Nos. 4,816,397 and 4,816,567.

Vectors are used to simplify manipulation of the DNA which encodes the HIV gp120 gene polypeptide, either for preparation of large quantities of DNA for further processing (cloning vectors) or for expression of the HIV gp120 gene. polypeptide (expression vectors). Vectors comprise plasmids, viruses (including phage), and integratable DNA fragments, i.e., fragments that are, integratable into the host genome by recombination. Cloning vectors need not contain expression control sequences. However, control sequences in an expression vector include transcriptional and translational control sequences such as a transcriptional promoter, a sequence encoding suitable ribosome binding sites, and sequences which control termination of transcription and translation. The expression vector should preferably include a selection gene to facilitate the stable expression of HIV gp120 gene and/or to identify transformants. However, the selection gene for maintaining expression can be supplied by a separate vector in cotransformation systems using eukaryotic host cells.

Suitable vectors generally will contain replicon (origins of replication, for use in non-integrative vectors) and control sequences which are derived from species compatible with the intended expression host. By the term "replicable" vector as used herein, it is intended to encompass vectors containing such replicons as well as vectors which are replicated by integration into the host genome. Transformed host cells are cells which have been transformed or transfected with vectors containing HIV gp120 gene encoding DNA. The expressed HIV gp120 will be secreted into the culture supernatant, under the control of suitable processing signals in the expressed peptide, e.g. homologous or heterologous signal sequences. Only secreted proteins are fully glycosylated and fully capable of CD4 binding. See Fennie et al., *J. Virol.* (1989) 63: 639–646.

Expression vectors for host cells ordinarily include an origin of replication, a promoter located upstream from the HIV gp120 gene coding sequence, together with a ribosome binding site, a polyadenylation site, and a transcriptional termination sequence. Those of ordinary skill will appreciate that certain of these sequences are not required for expression in certain hosts. An expression vector for use with microbes need only contain an origin of replication recognized by the host, a promoter which will function in the host, and a selection gene.

Commonly used promoters are derived from polyoma, bovine papilloma virus, CMV (cytomegalovirus, either murine or human), Rouse sarcoma virus adenovirus, and simian virus 40 (SV40). Other control sequences (e.g., terminator, polyA, enhancer, or amplification sequences) can also be used.

An expression vector is constructed so that the HIV gp120 gene coding sequence is located in the vector with the appropriate regulatory sequences, the positioning and orientation of the coding sequence with respect to the control sequences being such that the coding sequence is transcribed and. translated under the "control" of the control sequences (i.e., RNA polymerase which binds to the DNA molecule at the control sequences transcribes the coding sequence). The control sequences may be ligated to the coding sequence prior to insertion into a vector, such as the cloning vectors described above. Alternatively, the coding sequence can be cloned directly into an expression vector which already contains the control sequences and an appropriate restriction site. If the selected host cell is a mammalian cell, the control sequences can be heterologous or homologous to the HIV gp120 gene coding sequence, and the coding sequence can either be genomic DNA containing introns or cDNA.

Higher eukaryotic cell cultures may be used, whether from vertebrate or invertebrate cells, including insects, and the procedures of propagation thereof are known. See, for example, *Tissue Culture*, Academic Press, Kruse and Patterson, editors (1973).

Suitable host cells for expressing HIV gp120 gene in higher eukaryotes include: monkey kidney CVI line transformed by SV40 (COS-7, ATCC CRL 1651); baby hamster kidney cells (BHK, ATCC CRL 10); Chinese hamster ovary-cells-DHFR (described by Urlaub and Chasin, PNAS (USA) 77: 4216 (1980)); mouse Sertoli cells (TM4, Mather, J. P., *Biol. Reprod.* 23: 243–251 (1980)); monkey kidney cells (CVI ATCC CCL 70); African green monkey kidney cells (VERO76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060652, ATCC CCL 51); rat hepatoma cells (HTC, MI, 54, Baumann, M., et al., *J. Cell Biol.* 85: 1–8 (1980)) and TRI cells (Mather, J. P., et al., *Annals N.Y. Acad. Sci.* 383: 44–68 (1982)).

It will be appreciated that when expressed in mammalian tissue, the recombinant HIV gp120 gene product may have higher molecular weight due to glycosylation. It is therefore intended that partially or completely glycosylated forms of HIV gp120 having molecular weights somewhat different from 120 kD are within the scope of this invention.

Other preferred expression vectors are those for use in eucaryotic systems. An exemplary eucaryotic expression system is that employing vaccinia virus, which is well-known in the art. See. e.g., Macket et al. (1984) J. Virol. 49:857; "DNA Cloning," Vol. II, pp. 191–211, supra; PCT Pub. No. WO 86/07593. Yeast expression vectors are known in the art. See, e.g., U.S. Pat. Nos. 4,446,235; 4,443,539; 4,430,428; see also European Pub. Nos. 103,409; 100,561; 96,491. Another preferred expression system is vector pHSI, which transforms Chinese hamster ovary cells. See PCT Pub. No. WO 87/02062. Mammalian tissue may be cotransformed with DNA encoding a selectable marker such as dihydrofolate reductase (DHFR) or thymidine kinase and DNA encoding HIV gp120. If wild type DHFR gene is employed, it is preferable to select a host cell which is deficient in DHFR, thus permitting the use of the DHFR coding sequence as marker for successful transfection in hgt medium, which lacks hypoxanthine, glycine, and thymidine. An appropriate host cell in this case is the Chinese hamster ovary (CHO) cell line deficient in DHFR activity, prepared and propagated as described by Urlaub and Chasin, 1980, *Proc. Nat. Acad. Sci.* (USA) 77: 4216.

Depending on the expression system and host selected, HIV gp120 is produced by growing host cells transformed by an exogenous or heterologous DNA construct, such as an expression vector described above under conditions whereby the HIV gp120 protein is expressed. The HIV gp120 is then isolated from the host cells and purified. If the expression system secretes HIV gp120 gene into growth media, the protein can be purified directly from cell-free media as described. The selection of the appropriate growth conditions and initial crude recovery methods are within the skill of the art.

Once a coding sequence for HIV gp120 has been prepared or isolated, it can be cloned into any suitable vector and thereby maintained in a composition of cells which is substantially free of cells that do not contain a HIV gp120 gene coding sequence (e.g., free of other library clones). Numerous cloning vectors are known to those of skill in the art. Examples of recombinant DNA vectors for cloning and host cells which they can transform include the various bacteriophage lambda vectors (*E. coli*), pBR322 (*E. coli*), pACYC177 (*E. coli*), pKT230 (gram-negative bacteria), pGV1106 (gram-negative bacteria), pLAFRI (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), actinophage, fC31 (Streptomyces), YIpS (Saccharomyces), YCpl9 (Saccharomyces), and bovine papilloma virus (mammalian cells). See generally, DNA Cloning: Vols. I & II, supra; T. Maniatis et al., supra; B. Perbal, supra.

Site-directed mutagenesis for insertion of cleavage sites (when desired) is conducted using a primer comprising a synthetic oligonucleotide complementary to a single-stranded phage DNA to be mutagenized, except for limited mismatching representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are hybridized with kinased synthetic primer at a temperature which permits hybridization of an exact match, but at which the mismatches with the original strand are sufficient to prevent hybridization. Plaques which hybridize with the probe are then picked, cultured, and the DNA recovered.

A general method for site-specific incorporation of unnatural amino acids into proteins is described in Christopher J. Noren, Spencer J. Anthony-Cahill, Michael C. Griffith, Peter G. Schultz, (April 1989), Science, Vol 244, pp 182–188. This method may be used to create analogs with unnatural amino acids.

Although the purification aspect of the invention can be carried out on a cell medium containing fetal calf serum, which is typically used in growing mammalian cells, is preferred to use a culture medium containing relatively small amounts of FCS. For example, COS cells transfected with a plasmid construct containing the gp120 gene can be used as a source of gp120. Such cells transiently expressing gp120 can be grown in Delbecco's modified essential medium (DMEM) with or without antibiotics, sodium pyruvate, glutamine, and 1% (instead of the normal 5–6%) fetal calf serum. Pooled cell culture media from various time intervals after transfection can be subjected to the purification process of the present invention.

The expression system used experimentally by the present inventors for expression of gp120 is described fully in U.S. patent application Ser. No. 138,894, filed Dec. 24, 1987 (herein incorporated by reference). The specific vectors used are identified as pCMV6a120-SF2 (referred to as pCMV6ARV120tpa in U.S. Ser. No. 138,894) and Ad-dhfr. The vectors were used to transfect a CHO cell line to give the gp120 producer identified as CHO-A-6a120-145.0.1-22. No advantage is seen in the use of this cell line over other gp120 produces prepared by other techniques.

It should be recognized that no specific method, cell line, or genetic isolate of virus used for producing gp120 in its crude form is preferred by the present inventors over any other technique. It is contemplated that the present purification technique will produce conformation-retained gp120 from any source that contains full-length, glycosylated, non-fused gp120. The specific examples relating to gp120 production in the Examples section that follows result from decisions that were in many cases made for convenience only. Specific genetic material, cell lines, growth conditions, and the like were selected from those most familiar and readily available to the inventors, and the present inventors believe that any of the gp120 sources described in the scientific literature or later developed can be used equally well in the practice of the present purification process.

Sources of CD4 Peptide for use as gp120/CD4 Binding Standards

CD4 molecules useful for testing whether gp120 compositions have the binding properties described herein can be prepared in a varieties of manners, including isolation from natural resources and by techniques of genetic engineering. A soluble human CD4 fragment capable of binding to the gp120 molecule is described PCT application No. 8903222, published Apr. 20, 1989, and filed Oct. 5, 1988. Modified CD4 molecules exhibiting gp120 binding are described in PCT application No. 8902922, published Apr. 6, 1989, and filed Oct. 3, 1988. A CD4-secreting cell line similar to the one used as a source in preparing the CD4 used in the Examples that follow can be obtained from the ERC Bio-Services Corporation, 649A Lofstrand Lane, Rockeville, Md. 20850, USA and is listed as cell line CHO ST4.2 in the January 1990 edition of the AIDS Research and Reference Reagent Program Catalog published by the National Institutes of Health of the U.S.D.H.H.S. Other sources of CD4 and purification techniques are described in, for example, Smith et al., *Science* (1987) 238:1704–1707; Lasky et al., *Cell* (1.987) 50:975–985; Maddon et al., *Cell* (1985)., 42:93–104; and Littman et al., *Nature* (1987) 325:453–455. Purification of CD4 from cell media typically involves binding of CD4 (and other carbohydrate-containing molecules) to conconvalin A coupled to a solid support such as Sepharose 4B followed by ion exchange chromatography. Further, purification by affinity chromatography using a monoclonal antibody specific for the CD4 molecule can take place if desired. Unlike gp120, no problems are apparent in using affinity chromatography to purify CD4.

Uses of gp120 of the Invention

Although one important use of the conformation-retained gp120 of the present invention is as a vaccine, a number of other utilities also exist. For example, the conformation-retained gp120 is particularly useful in preparing anti-id antibodies that match the binding site on the gp120 molecule for the CD4 molecule. Other uses include as standards in competitive binding assays for the presence of HIV-1 virus particles. Indeed, the gp120 glycoprotein of the present invention can be used in any manner in which the gp120 molecules previously available have been used, although it will more closely resemble gp120 in the form in which it is naturally found in virus particles.

One obvious utility of gp120 composition of the present invention is in immunoassay for either anti-HIV antibodies or for HIV polypeptides, particularly anti-gp120 antibodies and vital gp120. Design of immunoassays is subject to a great deal of variation in the art. Thus, the following discussion is only illustrative, not inclusive. See generally, however, U.S. Pat. Nos. 4,743,678; 4,661,445; and 4,753, 873 and EPO Publication Number 181,150 and 216,191.

An immunoassay for viral gp120 may use, for example, a monoclonal antibody directed towards a viral epitope, a combination of monoclonal antibodies directed towards epitopes of viral gp120, polyclonal antibodies directed towards the viral gp120, or a combination of monoclonal and polyclonal antibodies.

Immunoassay protocols may be based, for example, upon composition, direct reaction, or sandwich-type assays. Protocols may also, for: example, be heterogeneous and use solid supports, or may be homogeneous and involve immune reactions in solution. Most assays involved the use of labeled antibody or polypeptide. The labels may be, for example, fluorescent, chemiluminescent, radioactive, or dye molecules. Assays which amplify the signals from the probe are also known examples of such assays are those which utilize biotin and avidin, and enzyme-labeled and mediated immunoassays, such as ELISA assays.

Typically, an immunoassay for anti-HIV antibody will involved selecting and preparing the test sample, such as a biological sample, and then incubating it with a gp120 composition of the present invention under conditions that allow antigen-antibody complexes to form. Such conditions are well known in the art. In a heterogeneous format, for example, the gp120 is bound to a solid support to facilitate separation of the sample from the polypeptide after incubation. Examples of solid supports that can be used are nitrocellulose, in membrane or microtiter well form, polyvinylchloride, in sheets or microtiter wells, polystyrene latex, in beads or microtiter plates, polyvinlyidine fluoride, known as Immobulon®, diazotized paper, nylon membranes, activated beads, and Protein A beads. Most preferably, Dynatech, Immulon® 1 microtiter plates or 0.25 inch polystyrene beads, Spec finished by Precision Plastic Ball, are used in the heterogeneous format. The solid support is typically washed after separating it from the test sample. In homogeneous format, on the other hand, the test sample is incubated with the gp120 antigen in solution, under conditions that will precipitate any antigen-antibody complexes that are formed, as is known in the art. The precipitated complexes are then separated from the test sample, for example, by centrifugation the complexes formed comprising anti-HIV antibody are then detected by any number of techniques. Depending on the format, the complexes can be detected with labeled anti-Xenogenic Ig or, if a competitive format is used, by measuring the amount of bound, labeled competing antibody.

In immunoassays where viral gp120 polypeptides are the analyte, the test sample, typically a biological sample, is incubated with anti-gp120 antibodies again under conditions that allow the formation of antigen-antibody complexes. Various formats can be employed, such as "sandwich" assay where antibody bound to a solid support is incubated with the test sample; washed, incubated with a second, labeled antibody to the analyte; and the support is washed again. Analyte is detected by determining if the second antibody is bound to the support. In a competitive format, which can be either heterogeneous or homogeneous, a test sample is usually incubated with an antibody and a labeled competing antigen, either sequentially or simultaneously. These and other formats are well known in the art.

When used in a vaccine, the gp120 glycoprotein of the present invention is sometimes referred to as a "subunit" vaccine, as gp120 is a subunit of the HIV virus. As such it offers significant advantages over traditional vaccines in terms of safety and cost of production; however, subunit vaccines are often less immunogenic than whole-virus vaccines, and it is expected that adjuvants with significant immunostimulatory capabilities will be required in order to reach their full potential in preventing disease. However, all adjuvants tested to date have shown ability to induce formation of multi-isolate neutralizing antibodies when used with the conformation-retained gp120 of the invention, so that specific adjuvants are not part of the broader aspects of the present invention. Certain adjuvants, however, are preferred because of their own advantageous properties.

Currently, the only adjuvants approved for human use in the United States are aluminum salts (alum). These adjuvants have been useful for some vaccines including hepatitis B, diphtheria, polio, rabies, and influenza.

Complete Freund's Adjuvant (CFA) is a powerful immunostimulatory agent that has been used successfully with many antigens on an experimental basis. CFA is comprised of a mineral oil, an emulsifying agent such as Arlacel A, and killed mycobacteria such as *Mycobacterium tuberculosis*. Aqueous antigen solutions are mixed with these components to create a water-in-oil emulsion. CFA causes severe side effects, however, including pain, abscess formation, and fever, which prevent its use in either human or veterinary vaccines. The side effects are primarily due to the patient's reactions to the mycobacterial component of CFA.

Incomplete Freund's Adjuvant (IFA) is similar to CFA without the bacterial component. While not approved for use in the United States, IFA has been useful for several types of vaccines in other countries. IFA has been used successfully in humans with influenza and polio vaccines and with several animal vaccines including rabies, canine distemper, and hoof-and-mouth disease. Experiments have shown that both the oil and emulsifier used in IFA can cause tumors in mice, indicating that an alternative adjuvant would be a better choice for human use.

Muramyl dipeptide (MDP) represents the minimal unit of the mycobacterial cell wall complex that generates the adjuvant activity observed with CFA (see Ellouz et al. (1974) *Biochem. Biophys. Res. Comm.*, 59: 1317). Many synthetic analogues of MDP have been generated that exhibit a wide range of adjuvant potency and side effects (reviewed in Chedid et al. (1978) *Prog. Allergy*, 25: 63). Three analogues that may be especially useful as vaccine adjuvants are threonyl derivatives of MDP (see Byars et al. (1987) *Vaccine*, 5: 223), n-butyl derivatives of MDP (see Chedid et al. (1982) *Infect and Immun.*, 35: 417), and lipophilic derivatives of muramyl tripeptide (see Gisler et al (1981) *Immunomodulations of Microbial Products and Related Synthetic Compounds*, Y. Yamamura and S. Kotani, eds., Excerpta Medica, Amsterdam, p. 167). These compounds effectively stimulate humoral and cell-mediated immunity and exhibit low levels of toxicity.

One promising lipophilic derivative of MDP is N-acetylmuramyl-L-alanyl-D-isoglutamyl-L-alanine-2-[1,2-dipalmitoyl-sn-glycero-3-(hydroxyphosphoryloxy)]ethylamide (MTP-PE). This muramyl peptide has phospholipid tails that allow association of the hydrophobic portion of the molecule with a lipid environment while the muramyl peptide portion associates with the aqueous environment. Thus the MTP-PE itself can act as an emulsifying agent to generate stable oil-in-water emulsions.

In experiments on mice, MTP-PE has been shown to be effective as an adjuvant in stimulating anti-HSV gD antibody titers against Herpes simplex virus gD antigen, and that effectiveness was vastly improved if the MTP-PE and gD were delivered in oil (IFA) rather than in aqueous solution. Since IFA is not approved for human use, other oil delivery systems have been investigated for MTP-PE and antigen. An emulsion of 4% squalene with 0.008% Tween 80 and HSV gD gave very good results in the guinea, pig. This formulation, MTP-PE-LO (low oil), was emulsified by passing through a hypodermic needle and was quite unstable.

Nevertheless, MTP-PE-LO gave high antibody titers in the guinea pig and good protection in a HSV challenge of immunized guinea pigs (see Sanchez-Pescador et al. (1988) *J. Immunology,* 141: 1720–1727 and *Technological Advances in Vaccine Development* (1988) Lasky et al., eds., Alan R. Liss, Inc., p. 445–469). The MTP-PE-LO formulation was also effective in stimulating the immune response to the yeast-produced HIV envelope protein in guinea pigs. Both ELISA antibody titers and virus neutralizing antibody titers were stimulated to high level with the MTP-PE formulation. However, when the same formulation was tested in large animals, such as goats and baboons, the compositions were not as effective. Nevertheless, this system represents a potential adjuvant system for use with gp120 antigen.

Experiments have also demonstrated that an adjuvant composition comprising a metabolizable oil and an emulsifying agent, wherein the oil and emulsifying agent are present in the form of an oil-in-water emulsion having oil droplets substantially all of which are less than 1 micron in diameter, is an effective adjuvant composition to increase the efficiency of vaccines. Investigations have shown a surprising superiority of such adjuvant compositions over adjuvant compositions containing oil and emulsifying agents in which the oil droplets are significantly larger. These superior adjuvant compositions are the subject of a separate patent application EPO 0 399 843 publication the disclosure of which is herein incorporated by reference.

The adjuvant formulations are generally prepared from the ingredients described above prior to combining the adjuvant with the gp120 antigem. The gp120 antigen, on gaining access to the tissue of an animal stimulates the formation of specific antibodies and reacts specifically in vivo or in vitro with such an antibody. Moreover, the antigen stimulates the proliferation of T-lymphocytes with receptors for the antigen and can react with the lymphocytes to initiate the series of responses designated cell-mediated immunity.

The formulation of a vaccine of the invention will employ an effective amount of the gp120 antigen. That is, there will be included an amount of antigen which, in combination with the adjuvant, will cause the subject to produce a specific and sufficient immunological response so as to impart protection to the subject from subsequent exposure to an HIV virus.

One preferred adjuvant formulation, designated MF-59, comprises 0.5% Tween-80, 0.5% Span, 5.0% squalene in an MTP-PE solution containing 0.40 micrograms/ml MTP-PE. The emulsion composition is passed 10 times through a Microfluidizer at 10,000 psi at 0° C. The resulting material is passed through a 0.2 micron filter and stored under argon at 4° C.

No single dose designation can be assigned which will provide specific guidance for each and every gp120 formulation which may be employed as a vaccine. The effective amount of antigen will be a function of its inherent activity and purity, which will vary from isolate to isolate. Guidance as to initial proportions of components of the vaccine formulations can be obtained from the Examples section, which show various formulations that have proven effective is stimulating neutralizing antibodies. These proportions will be adjusted for individual preparations of conformation-retained gp120 natural, as is well understood in the art.

The vaccine compositions of the invention are useful for both the prevention of HIV-1 infection. While all animals that can be afflicted with HIV-1 can be treated in this manner, the invention, of course, is particularly directed to the preventive and therapeutic use of the vaccines of the invention in man. Often, more than one administration may be required to bring about the desired prophylactic or therapeutic effect; the exact protocol (dosage and frequency) can be established by standard clinical procedures. The vaccine compositions are administered in any conventional manner which will introduce the vaccine into the animal, usually by injection. For oral administration the vaccine composition can be administered in a form similar to those used for the oral administration of other proteinaceous materials, such as insulin. As discussed above, the precise amounts and formulations for use in either prevention or therapy can vary depending on the circumstances of the inherent purity and activity of the antigen, any additional ingredients or carders, the method of administration and the like. By way of non-limiting illustration, the vaccine dosages administered will typically be, with respect to the gp120 antigen, a minimum of about 0.1 mg/dose, more typically a minimum of about 1 mg/dose, and often a minimum of about 10 mg/dose. The maximum dosages are typically not as critical. Usually, however, the dosage will be no more than about 1 mg/dose, typically no more than 500 mg/dose, often no more than 250 mg/dose. These dosages can be suspended in any appropriate pharmaceutical vehicle or carder in sufficient volume to carry the dosage. Generally, the final volume, including carriers, adjuvants, and the like, typically will be at least 0.1 ml, more typically at least about 0.2 ml. The upper limit is governed by the practicality of the amount to be administered, generally no more than about 0.5 ml to about 1.0 ml.

In view of the above, the invention also include a method of use of the vaccine compositions of the invention for the prevention of an HIV-1 infection in an animal and a method of use of the vaccine compositions of the invention for the therapeutic treatment of animals already infected with HIV-1. Animals include mammals, such as primates, for example chimpanzees, baboons and humans.

The invention now being generally described, the same would be better understood by reference to the following detailed examples which are set forth for purposes of illustration only and are not to be considered limiting of the invention unless as specified.

EXAMPLE 1

Mutagenesis and Expression of HIV gp120 in Mammalian Cells

The envelope gene encoding gp160 of HIV-SF2 was engineered for expression of gp120 sequences by the introduction of a stop codon following Arg509 at the gp120 natural -gp41 processing site. The 5' end of the gene was modified to insert an NheI restriction endonuclease site 5' to the sequences encoding Glu31. so that the natural signal sequence could be replaced by other signal sequences to test for improved secretion from mammalian cells. In order to produce gp120 as a secreted glycoprotein in mammalian cells, the HIV signal sequence and 5' untranslated sequences were replaced with those from human t-PA, mutagenized to place an NheI site near the 3' end of the tPA signal DNA to encode Ala Ser. The resulting gene construct was fused to a series of promoters. Transient expression of gp120 was evaluated was evaluated following transfection of the expression vectors in COS-7 cells and comparisons of levels of secreted gp120 by goat-capture ELISA (described below) and western blot. Highest levels of expression were seen using the CMV IE-1 promoter, at least 50-fold higher than with the SV40 early promoter. For construction of permanent cell lines the expression plasmid pCMV6aSF2–120

(FIG. 1) was cotransfected with a dhfr expression plasmid using calcium phosphate coprecipitation into CHO dhfr-cells (dg44; see below). The resulting cell lines were characterized by screening clones with the gp120 goat-capture ELISA. Highest expressing cell lines were amplified in methotrexate in pools. Clones were isolated at the 0.1 mM level. Using purified protein as a standard, cell lines were shown to be secreting gp120 in the mg per liter range at the T flask level.

The cells used for expression of the gp120 gene were originally obtained by Dr. Leslie Rail of Chiron Corporation, in September, 1985, at approximately 100 passages. These cells were originally isolated by Dr. Gail Urlaub and Dr. Lawrence Chasin at Columbia University, New York and are described in Urlaub et al., Cell (1983) 33: 45. The cells were designated as DG44. They are derived from Chinese hamster ovary (CHO) K-1 cells that were made dihydrofolate reductase deficient (dhfr⁻) by virtue of a double deletion.

The CHO dhfr⁻ cells were cultured continuously in the following medium: Hams F-12 medium supplemented with 10% dialyzed fetal calf serum, 200 mg/mL of streptomycin. The medium and serum were obtained from the University of California, San Francisco Cell Culture Facility, San Francisco, Calif. All other ingredients were supplied by Sigma Chemical Co., St. Louis, Mo. Cells were maintained by passaging two times a week with a 1:10 split in T-75 flasks.

For storage, aliquots of cells were frozen in fetal calf serum (FCS), 10% dimethyl sulfoxide (DMSO) and stored at −80RC in the gas phase of liquid nitrogen. For this purpose, T75 flasks of cells were grown to confluency (approximately $10^7$ cells per T-75 flask). Cells were trypsinized, centrifuged and resuspended in ice-cold 10% DMSO in FCS at a concentration of about $5 \times 10^5$ cells/mL. One mL aliquots were transferred to cryopreservative vials. When cells were required, an aliquot was thawed in a 37RC water bath and cells were seeded in T-75 flasks for continuous culturing and passage.

The two assays used as described above for detecting HIV-1 envelope-related antigens were carded out in the following manner. For both assays, purified CHO-derived gp120 was used as a standard, using two-fold dilutions from 200 ng/ml to 0.195 ng/ml.

(a) Goat Capture ELISA:

The capture reagent for this assay was protein-A-Sepharose-affinity-purified immunoglobulin from a goat that had been hyperimmunized with purified env-2-3 (SF2), which is described below, a non-glycosylated polypeptide produced in yeast corresponding the amino acid sequence of gp120 of the HIV-SF2 virus isolate. The reagent used to detect captured antigen was a polyclonal antiserum raised in rabbits to the same antigen. Plates were coated with 5 mg/mL of goat immunoglobulin to env-2-3 (SF2), incubated with dilutions of viral lysate or mammalian-derived gp120 antigens and then the captured antigen detected by the rabbit polyclonal antiserum to env-2-3 (SF2) diluted 1/100 followed by conjugate and ABTS substrate.

(b) Human Capture ELISA:

This assay is identical to the "goat capture ELISA" described in a above except that the capture reagent was protein-A-Sepharose-purified immunoglobulin from human sera obtained from HIV-1 seropositive blood donors.

EXAMPLE 2

Cellular Production

One cell line, CHO-A-6a120-145-0.1-22, obtained as described in Example 1, was chosen for production in roller bottles in media with reduced serum and no methotrexate. Roller bottle cultures (850 $cm^2$) were established and expanded to confluency in medium (Delbecco's Modified Eagle's Medium and Ham's F-12, 1:1) supplemented with 6% fetal calf serum (FCS). For production, supplementation was switched to 1% FCS with 0.03% HB-CHO (Hana Biologics, Alameda, Calif.). Conditioned medium (200 ml) was collected every 24–48 hours, stored at 2–8C., pooled and clarified by filtration through 0.45 micron capsule filters (Gelman). Cells were maintained for more than two months in each of two production runs with no apparent loss of production of gp120. Expression levels ranged from 5 to 20 mg/L.

EXAMPLE 3

Purification (1) Concentration.

Concentration of the cell culture supernatant from Example 2 (40 L) was carried out using dead-end filtration (0.45 micron capsule filter, Gelman) and cross-flow ultrafiltration using a 30K cutoff hollow fiber ultrafilter (AG Technology #UFP-30-C-6; 6 $ft.^2$ and 0.5 mm fiber i.d.) driven by a positive displacement pump (Waukesha #18). Permeation rate was approximately 150 ml/min at a recirculation rate of approximately 12 L/min and a pressure of 26 psi. Filtration continued until the retentate volume, reached 1–2 L. The filtration steps were carried out in a cold room at 2°–8° C. The ultrafiltration concentrate was a brown, clear liquid.

(2) DEAE Chromatography.

The concentrate was applied to an ion exchange column (11.4 cm diam×15 cm) packed with DEAE Sephadex A-50 (Pharmacia) was equilibrated in Buffer (0.02M Tris-Cl, pH 8.0, 0.1M NaCl) at a flow rate of 35 ml/min at room temperature. The ultrafiltration concentrate was brought to a volume of 2 L and a conductivity of 1.4 mS by addition of sodium chloride (4M stock solution). The unadsorbed fraction containing the product was collected in 250 ml fractions using an Isco Foxy® fraction collector. Serum albumin, other proteins and the bulk of the brown colored material bound to the column and were eluted with a step gradients of 1M NaCl. These fractions contained a small but variable amount of product; no attempt was made to recover product from the bound fraction. The DEAE Sephadex A-50 resin was discarded after each use. The pass-through fraction has been shown to contain the bulk of the product by ELISA assay. At this stage of purity it was difficult to locate the diffuse gp120 band on an SDS gal.

(3) Phenyl Hydrophobic Interaction Chromatography.

Figure 3A:
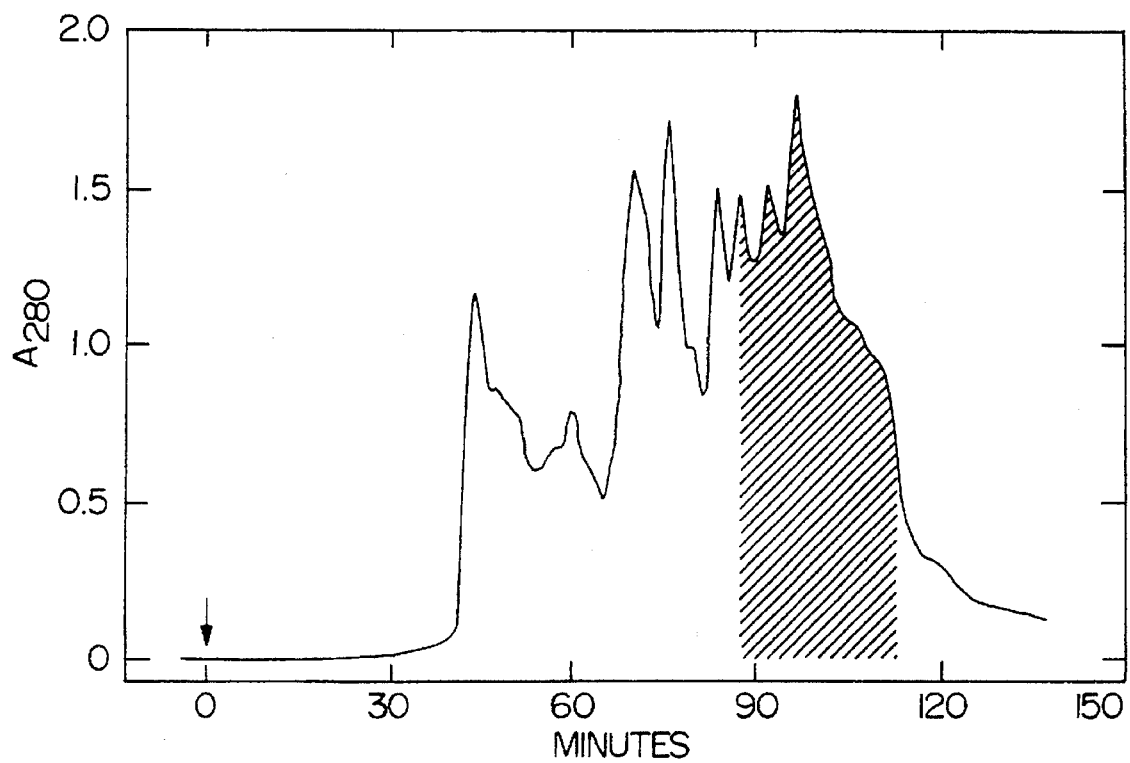
FIG. 3A is a graph showing product fractions as obtained in a purification step using a phenyl HIC column.

The DEAE fraction was brought to 40% saturation in ammonium sulfate by addition of solid ammonium sulfate. After thorough mixing a small amount of precipitate was removed by centrifugation. A TSK Phenyl-5PW HIC column (5.5 cm diam ×20 cm) was washed with at least two volumes of water using a Gilson preparative HPLC. Then the column was equilibrated with two or more volumes of Buffer A (0.02M sodium acette, pH 5.0, 40%-saturated ammonium sulfate). Column equilibration was verified by conductivity measurement of the effluent. The supernatant fraction after addition of ammonium sulfate was applied to the column by pumping through Pump A at 30 ml/min, then the column was washed with Buffer A until the baseline stabilized (usually about 15–20 min). A gradient was run to 0.02M sodium acetate, pH 5.0, over 40 min to elute the product. Fractions under the OD peak were assayed by SDS gel electrophoresis using a Pharmacia PHAST® system to locate the product. At this stage of purity the gp120 band was clearly discernible. Product-containing fractions were pooled for the next stage of chromatography (see FIG. 3A).
(d) Ether Hydrophobic Interaction Chromatography.

Figure 3B:
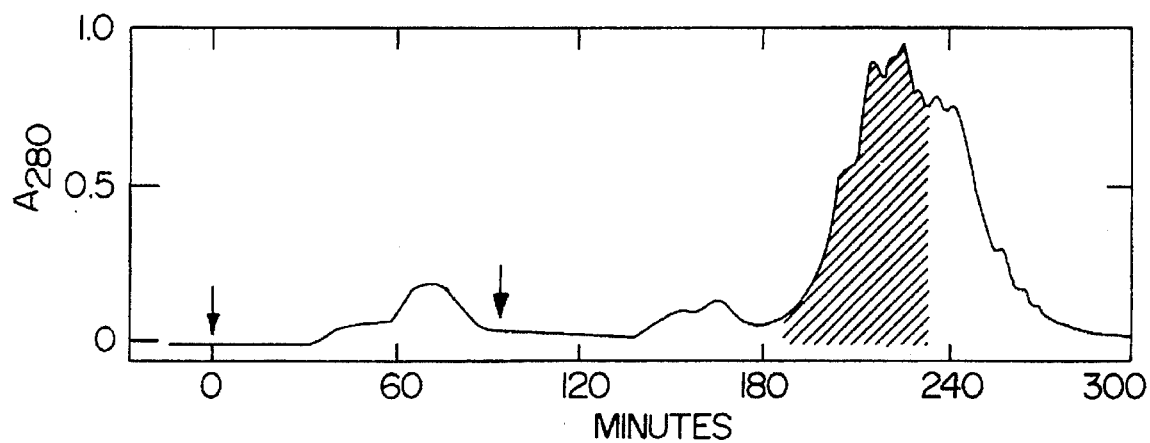
FIG. 3B is a graph showing product fractions as obtained is a purification step using an ether HIC column.
Figure 3C:
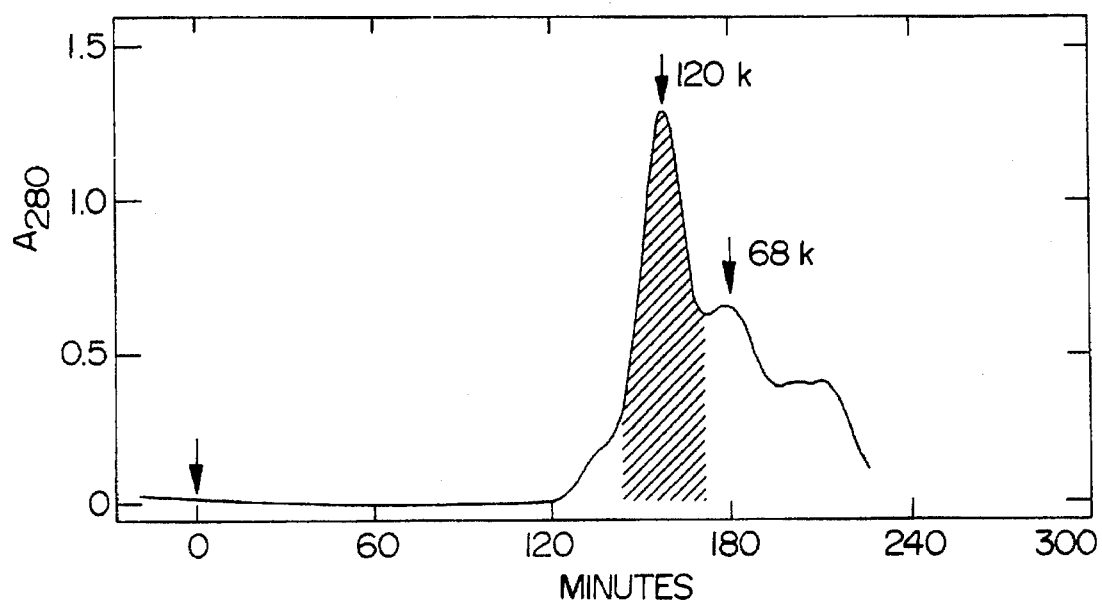
FIG. 3C is a graph showing product fractions as obtained in a purification step using gel filtration chromatography.

A second HIC step was carried out on a TSK Ether-5PW HPLC column (5.5 cm diam×20 cm) following the same procedure used for the phenyl HIC column. The column was washed with at least two column volumes of water, then equilibrated in Buffer A (40%-saturated ammonium sulfate, 0.02M sodium acetate, pH 5.0). The product pool from the phenyl column was brought to a conductivity of 165 S/cm by addition of ammonium sulfate, followed by centrifugation for 10 min at 12,000 rpm. The sample was loaded and eluted as described above using a 40 min gradient from 100% Buffer A to 100% Buffer B. Product-containing fractions (see FIG. 3B) were located by SDS gel electrophoresis on a PHAST® system, then pooled for gel filtration chromatography. The gp120 peak from the ether column was mainly gp120 with smaller amounts of lower molecular weight contaminants. These contaminants were resolved by gel filtration chromatography (below).

(5) Gel Filtration Chromatography.

The ether HIC fraction was concentrated on an ultrafiltration membrane (Amicon YM-30) to a protein concentration of approximately 10 mg/ml as measured by A-280 assuming an extinction coefficient of 0.6=1 mg/ml, then diafiltered against at least five volumes of 0.1M sodium phosphate, pH 6.9. Sample was applied to a gel filtration column (Superdex®200, Pharmacia, 1.6 cm diam×60 cm) at a total protein concentration of not more than 10 mg/ml in a volume of not more than 4% of the column volume and eluted with 0.1M sodium phosphate, pH 6.9. Fractions of 1 ml were collected, subjected to SDS gel electrophoresis with Coomassie Brilliant Blue R350 staining on a PHAST® System and to gel filtration HPLC on a DuPont GF-450 column (running buffer: 0.2M sodium phosphate, pH 6.7, 1 ml/min) to locate dimer-containing fractions, then pooled. The leading edge of the gp120 peak contained pure gp120 while the trailing edge was rechromatographed on the gel filtration column. The product pool was concentrated on an Amicon YM-30 membrane, diafiltered against 5 volumes of distilled water, and lyophilized for at least two days at a pressure of less than 10 microns.

(6) Summary of Purification Results.

Table 1 summarizes the results of a typical purification starting with 40 liters of cell culture supernatant. These data show that a 250-fold purification is achieved with a yield of 20–25%. The product appeared as a broad band migrating at H120 KD in an SDS gel. Densitometry revealed 80–90% of the staining intensity was under the gp120 band. This probably represents a minimum estimate of the purity of this preparation because gp120 binds stain poorly. Approximately 7-fold less Coomassie Brilliant Blue was bound per microgram protein compared to BSA. The appearance of the gel band was not altered by pretreatment of the sample with 2-mercaptoethanol or dithiothreitol, showing that the protein is not internally cleaved. Reverse phase HPLC analysis at elevated temperature also suggested that the purity of the product exceeded 90%.

TABLE 1

SF2 rgp120 Purification Table

| Step | Volume | Protein | rgp120 | Purity |
|---|---|---|---|---|
| 1. Culture Supernatant | 40.0L | 55.g | 210.mg | 0.4% |
| 2. UF Concentrate | 3.76 | 44.9 | 180 | 0.4 |

TABLE 1-continued

SF2 rgp120 Purification Table

| Step | Volume | Protein | rgp120 | Purity |
|---|---|---|---|---|
| 3. DEAE | 4.75 | 8.55 | 140 | 1.6 |
| 4. Phenyl HIC | 0.724 | 0.996 | 150 | 15 |
| 5. Ether HIC | 0.260 | 0.354 | 110 | 31 |
| 6. Gel Filtration | 0.020 | 0.053 | 48 | 90 |

EXAMPLE 4

(1) Comparison of Purified SF-2 rgp120 with Viral gp120.

Purified gp120 was subjected to SDS polyacrylamide gel electrophoresis to assess size and purity. The protein migrated at the predicted location for a 120K protein with a broadly staining band characteristic of glycoproteins. This broad band is consistent with expected carbohydrate heterogeneity at the 22 predicted N-linked glycosylation sites, which has been described for other isolates. To compare the recombinant gp120 with that found in virions, lysates of HIV-SF2-infected HUT-78 cells were prepared and examined by western blot with HIV-positive human and gp120specific animal sera. Patterns observed were consistent with conserved conformation.

(2) N-Terminal Sequencing.

The amino-terminal amino acid sequence was determined by automated Edman degradation. The observed and expected sequences were:

| observed | EKLWVTVYYGVPVWK ... |
|---|---|
| expected | TEKLWVTVYYGVPVWK ... |

This sequence confirms that the heterologous signal was correctly processed by the signal peptidase, following serine of the signal, and that the protein is not fused to any additional amino acids. This sequence lacks the N-terminal threonine found on viral gp120 from the HTLVIIIB isolate (Robey et al., PNAS (1986) 83: 7023–7027). The N-terminal amino acid sequence matches the HIV-SF2 envelope sequence predicted from the DNA sequence of this isolate for at least the first fifteen amino acids.

(3) Amino Acid Composition.

Amino acid analyses were performed on five lots of gp120 purified as described in Example 3. The average of these values agreed with the composition expected from the DNA sequencer within experimental error for all amino acids except ile (33.5 observed vs. 39 expected) and ser (32.7 observed vs 24 expected). The ser value was variable within the five lots and probably represents a serine-rich contaminant.

(4) Native Gel Electrophoresis and IEF.

Charge heterogeneity of gp120 was evident in isoelectric focusing experiments and in native gel electrophoresis. Isoelectric focusing revealed the presence of multiple bands within the envelope pH 5 to 7. The protein migrated as a single broad band in a nondenaturing polyacrylamide gel.

(5) Gel Filtration HPLC.

The molecular weight of recombinant gp120 was 120K in the presence of SDS; molecular weight in the absence of SDS was measured by gel filtration HPLC. At neutral pH in medium ionic strength buffers, purified gp120 eluted as a single major peak with a retention volume corresponding to a molecular weight of H130K. A small amount of dimer was also present; the fraction of dimer increased to 10–20 of the total gp120 upon storage in solution. The dimer fraction was isolated at the gel filtration step and analyzed separately. This fraction migrated as a monomer when analyzed by SDS gel electrophoresis in the presence of reducing agent but as a dimer in the absence of reducing agents (2-mercaptoethanol or dithiothreitol) so it was probably linked by disulfide bonds. The amino acid composition of the dimer fraction was indistinguishable from that of the monomer fraction. The dimer fraction also bound CD4 when tested by the radioimmune precipitation assay. The gp120 gel filtration HPLC peak was broader than one would expect for a protein of this molecular weight. The extra peak width obtained for gp120 can be attributed to heterogeneity in the carbohydrate moiety. The high molecular weight of gp120 relative to the impurities present made it possible to use gel filtration HPLC as a purification assay after the phenyl HIC step. It was routinely used as an assay at the gel filtration step to eliminate from the product pool the fractions containing gp120 dimers.

(6) CD4 Binding.

The CD4 used in this example was recombinant, soluble CD4 derived from a CHO cell line transfected with an expression plasmid encoding the full external domain. Details on CD4 production for use as a binding standard are set forth in Example 5. Binding experiments were done by radioimmune precipitation by gel filtration HPLC.

(a) General Techniques of Radioimmune Precipitations.

Confluent monolayers of cells producing (for example) gp120 were labelled in Dulbecco's modified Eagle medium without cysteine and methionine (cys-met-DME). Five ml of cys-met-DME with 100 mCi/ml each $^{35}S$ met and cys, were added to each T75 flask for 6–8 hours. Labelled samples were harvested, centrifuged to remove cells, and stored at −80C until use. Samples to be precipitated were adjusted to 1X lysis buffer [0.1M NaCl, 0.02M tris pH 7.5, 1 mM EDTA, 0.5% NP40, 0.5% deoxycholate, 0.1% bovine serum albumin (BSA), 1 mM phenyl methyl sulfonyl fluoride (PMSF), 17 mg/ml aprotinin]. Samples were precleared with one tenth volume normal goat serum for 30 minutes at 4C, followed by 30 minutes precipitation with Protein A Sepharose (PAS) (½ volume 20% suspension) at 4RC. Immunoglobulin from hyperimmunized animals or HIV-positive human serum samples was affinity purified using PAS by standard techniques. Sera were titrated for the best signal to noise ratio; most immunoglobulin fractions were used at 5–10 mg per sample. Immune precipitations were 1–12 hours at 4C, depending upon the volume of the sample, followed by 1 hour with PAS. All samples were adjusted to the same volume within an experiment The PAS was washed with lysis buffer without BSA, followed by 0.12M Tris pH7, and the pellets were solubilized in 1 Laemmli sample buffer, boiled, and applied to gels., Gels were treated with En$^3$Hance®, dried, and fluorographed.

(b) CD4 Binding By Radioimmune Precipitation.

CD4 was labelled with $^{35}S$ as described above, and the concentration of CD4 was determined using a capture ELISA employing a monoclonal antibody and polyclonal rabbit serum raised against CD4. For coprecipitation experiments, CD4 was added in increasing amounts to a fixed amount of gp120 (1 mg) to determine the saturating amount, and then coprecipitated with anti-gp120 antisera. This amount of CD4 was used for gp120 titration experiments. Labelled CD4 was precleared with normal serum, as described above. Following preclearing of the labelled component, CD4 and gp120 were complexed for 1 hour at 4C, then antibody against the unlabelled component was added (10 mg per sample) for 1 hour at 4RC. OKT4 was purchased from Ortho Diagnostics. PAS was added for 1 hour at 4RC, and the complexes were washed and prepared for electrophoresis as described above.

Gp120 pre- and post-purification were both effective in binding to CD4 by this assay, as shown by equivalent band intensities for equivalent amounts of added gp120. A non-glycosylated analog of gp120 produced in yeast (env 2–3; see U.S. patent application Ser. No. 138,894, filed Dec. 24, 1987) was unable to bind to CD4 in this assay. The dimeric form of gp120 isolated from the Superdex®200 column also bound CD4 by this assay. Saturation of binding was determined graphically. From the half-saturation levels a $K_d$ of 6.9 nM was measured.

(c) CD4 binding by Gel Filtration HPLC.

Purified gp120 and unlabeled CD4 were mixed in a volume of 60 ml containing 0.3M potassium phosphate, pH6.8. After mixing, a portion of the sample (45 ml) was injected onto a DuPont GF-450 gel filtration HPLC column with a Waters WISP 712 sample injector run in 0.4M potassium phosphate, pH 6.8 at 1 ml/min. The optical density was monitored at 215 nm and data was recorded using Waters Maxima 820® chromatography software.

Figure 4:
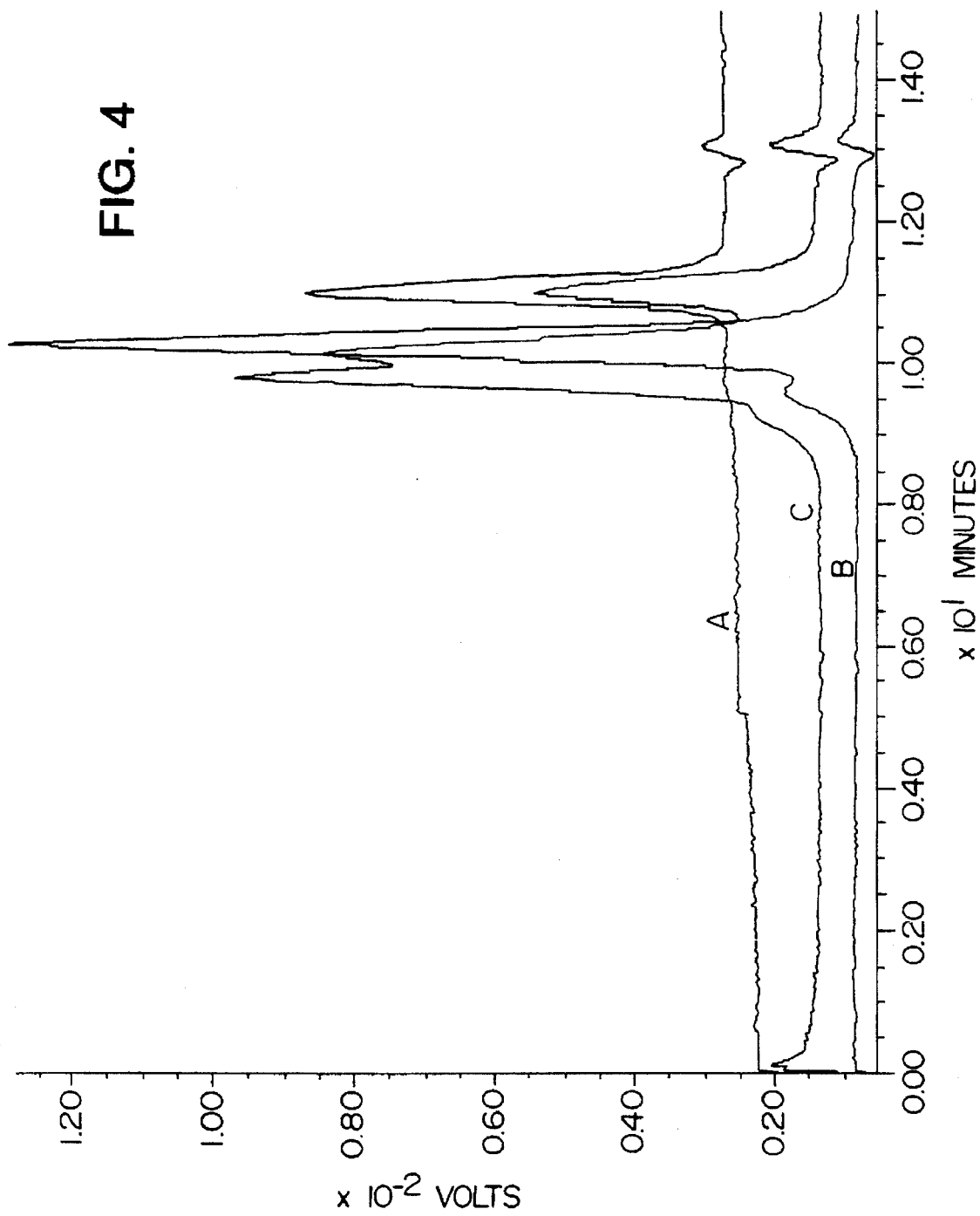
FIG. 4 is a graph showing formation of a CD4-gp120 complex using gel filtration HPLC.

When CD4 and gp120 were applied separately to a gel filtration HPLC column each component gave a single peak at the expected elution time (See FIG. 4; Trace A is CD4 alone, Trace B is gp120 alone). When the components were mixed together before chromatography, a new peak appeared at an elution time corresponding to 160K and the peaks at 120K and 40K diminished (FIG. 4; Trace C) This result provides direct physical evidence of the formation of a 1:1 complex between CD4 and gp120. Additional experiments were done with varying ratios of CD4 and gp120 and at different concentrations of the reactants. The results of these experiments supported the existence of a high affinity complex between one molecule of CD4 and one molecule of gp120.

EXAMPLE 5

CHO cells were cotransfected with AD-dhfr and an expression plasmid encoding soluble recombinant human CD4 (full external domain). The expression vector was constructed by cloning a CD-4-encoding sequence, a gift of Dr. D. Littman of UCSF, into the vector pCMV6a (pCMV6a120-SF2 minus the gp120 coding sequence). A cell line secreting soluble CD4 was isolated. The resulting cell line, identified as CHO ST4.2 is available publicly as previously described. The cloned gene, ST 4.2, encodes 380 amino acids corresponding to the four extracellular domains to the transmembrane boundary. The purification process for this protein involves two columns. First, the CHO cell supernatant was loaded onto and eluted from an S. Sepharose cation exchange column. One liter CHO supernatant was diluted to 15 L with double distilled water and loaded onto 300 ml swollen resin equilibrated in 0.2X PBS/2.5 mM EDTA, pH 7.0 (conductively 3.6 ohm$^{-1}$ cm$^{-1}$) at a load rate of 3.6 L/hr at room temperature. The column was rinsed with 500 mL 0.2X PBS/2.5 mM EDTA and 200 mL50 mM NaCl 0.2X PBS 12.5 mM EDTA. Elution was with 1 L 200 mM NaCl 10.2X PBS 12.5 mM EDTA. The eluate from this S. Sepharose column was then run over a monoclonal antibody affinity column. The monoclonal antibody (25-10-F5.5C1; hereafter referred to as 25–10-F5) used for this purification recognizes a conformational epitope in the amino-terminal half (within the first two immunoglobulin-like domains) of the extracellular region of CD4. Other antibodies with specificity for any epitope within the same domains should be equally effective. The S.

Sepharose eluent was filtered (0.45 micron) and loaded onto the affinity column at 1 ml/min or less. The loaded column was rinsed with distilled water (25X resin volume) and eluted with 5 mM triethylamine formate, 10 ml elution buffer per 4 ml of gel resin. The pH of the mAb eluent was adjusted to pH 7 with 1M Tris (pH 8.0). The fractions eluted from the affinity column were the dialyzed and concentrated. Table 1 shows the yield at each step of the purification procedure.

TABLE 1

Purification table for ST4.2 CD4 produced in genetically engineered CHO cells

| Fraction | Volume (ml) | Concentration (mg/liter) | Protein (mg) | mg CD4/ liter | mg CD4/ mg protein | Total CD4 (mg) | Yield (%) | Fold purification |
| --- | --- | --- | --- | --- | --- | --- | --- | --- |
| Supernatant | 486 | 1020 | 496 | 30.8 | 0.03 | 14.7 | — | 1 |
| S-sepharose eluate | 1000 | 11.9 | 11.9 | 11.12 | 0.93 | 11.12 | 76 | 31 |
| Affinity column eluate | 30 | 0.183 | 5.49 | 274 | 1.00 | 8.22 | 56 | 34 |
| Affinity column flow through | 1000 | N.D.[a] | N.D. | 0.05 | N.D. | 0.05 | 0.4 | — |

[a]N.D. = Not determined.

The levels of active CD4 in the various fractions were determined by using a capture ELISA employing the monoclonal antibody 25–10-F5 as the capture reagent and a rabbit polyclonal antisera raised against purified ST4.2 as the detecting reagent. The fractions and flow through from each column were compared to the initial supernatant and a known CD4 standard. This allowed quantitation of how much active CD4 was recovered at each step. It also allowed one to estimate the increase in purity following each step of the purification. This was done by comparing the total amount (milligrams) of active CD4, as determined by the ELISA, with total milligrams of protein, as determined by a Pierce protein microassay. Using these techniques the yield for the S. Sepharose column was shown to be 76% and the affinity column to be 74%, giving an overall yield of 56%. Note that the S. Sepharose column alone resulted in a 31-fold purification, yielding a solution that was 93% CD4 after just the first step. The affinity column increased the purity of the S. Sepharose eluent to essentially homogeneity.

The purity of these final fractions was analyzed in two ways. First, the protein was run on a 12% SDS gel and stained with Coomassie brilliant blue. This visual analysis indicated that the protein was highly purified; at least 95% of the final product was CD4. An amino acid analysis was performed on ST4.2 samples purified according to this protocol also indicated that the material was highly purified.

The gp120 binding ability of purified ST4.2 was analyzed both by ELISA and using a gp120 column. ST4.2 could be coated onto microtiter plates and would retain gp120 binding activity. To test gp120 binding of the various lots of CD4, microtiter plates were incubated with various concentrations of CD4 from each lot and then added a single concentration of gp120 to all wells. Bound gp120 was detected with a rabbit polyclonal antiserum to gp120 (Rb anti-env2-3 serum). A strong signal was seen which titered out as the amount of ST4.2 coated onto the plate decreased. Gp120 binding was also assessed for two of the lots by running the purified ST4.2 over an affinity column of gp120. An initial solution of 10 mg/ml ST4.2 was loaded on to the column. The CD4 content of each fraction was determined by immunoblot analysis of the various fractions utilizing the polyclonal rabbit antiserum to ST4.2 discussed above. These results indicated that close to 100% of the CD4 immunoreactive material was absorbed to the gp120 on the column matrix and eluted as a specific peak.

Native and denatured ST4.2 were coated onto microtiter plates and the ability of various CD4-specific immunological reagents to recognize the two forms of the protein Were compared. A rabbit polyclonal serum, prepared by immunization with purified ST4.2, recognized both native and denatured forms of CD4; OKT4A, which is known to recognize a conformational epitope, clearly reacted with native CD4, but did not react with the protein that had been denatured. The monoclonal antibody 25-10-F5 showed a pattern of reactivity similar to OKT4A.

Preparations of purified ST4.2 were stored at −80° C. and 4° C. and tested periodically for (1) immunoreactivity with the rabbit polyclonal antiserum that recognizes both native and denatured CD4, (2) recognition by OKT4A and 25-10-F5, which only react with native CD4 and (3) gp120 binding. A significant loss in activity assessed by OKT4A and 25-10-F5 monoclonal antibody as well as gp120 binding was observed upon storage at 4° C. However, the material stored at −80° C. retained full activity. In addition, it has also been noted that purified ST4.2 looses activity upon repeated freezing and thawing.

EXAMPLE 6

An immunization experiment was carried out to compare production of neutralizing antibodies using a gp120 composition of the invention with retained conformation to other gp120 molecules whose conformation is known to be modified. A gp120 analog (env 2-3) prepared in yeast, which is denatured and non-glycosylated, was used as a comparison antigen. Both gp120 materials were derived from the same gene source, HIV-1 SF-2 isolate. Antibody production was measured in baboons using the immunization schedule shown in Table 2.

TABLE 2

| Group # | Animal Number(s) | Adjuvant Name | Dose | Antigen Name | Dose | Volume Per Site | Sites Per Animal | Injection Route |
|---|---|---|---|---|---|---|---|---|
| 1 | (3) 2951,2953,2964 | MTP-PE in ICFA (SY) | 250 mg | gp120/SF2 | 55 mg | 0.5 mL | one | IM/thigh |
| 2 | (3) 2952,2957,2958 | MTP-PE in ICFA (SY) | 250 mg | env2-3/SF2 | 25 mg | 0.5 mL | one | IM/thigh |
| 3 | (3) 2949,2954,2966 | MTP-PE in S (MF/KE) | 250 mg | gp120/SF2 | 55 mg | 0.5 ml | one | IM/thigh |
| 4 | (3) 2950,2956,2967 | MTP-PE in S (MF/KE) | 250 mg | env2-3/SF2 | 25 mg | 0.5 ml | one | IM/thigh |
| 5 | (2) 2955, 2965 | Alum | 0.8 mg | gp120/SF2 | 55 mg | 0.5 ml | one | IM/thigh |
| 6 | (2) 2947, 2948 | Alum | 0.8 mg | env2-3/SF2 | 25 mg | 0.5 ml | one | IM/thigh |

Immunogens were prepared in the following manner:
(1) Groups 1 and 2: Add one part antigen (gp120 or env 2-3) to two parts incomplete Freund's Adjuvant (ICFA), mix by syringe, and inject 500 ml per animal.
(2) Groups 3 and 4: Warm vial of antigen/MTP-PE adjuvant to room-temperature, vortex for one minute, and inject 500 ml per animal within 30 minutes (re-mix as needed).
(3) Groups 5 and 6: Warm vial of antigen/alum to room-temperature, vortex for one minute, and inject 500 ml per animal within 30 minutes (re-mix as needed).

Immunization was carried out at the beginning of the experiment and at the 4th, 8th 12th and 20th week after start of the experiment. Blood samples were taken at the start of the experiment (pre-bleed) and at the times indicated in the tables (below) which report results.

The results are summarized in the attached Tables 3 and 4. The env 2-3-immunized animals show neutralizing activity against the homologous isolate, HIV-SF-2, in all adjuvant groups, and in one adjuvant group (IFA-MTP) neutralization against HIV-MN (3 of 7 animals total). There is one animal that shows detectable neutralization against HIV-HTLV-IIIB with this antigen.

In contrast, all of the gp120-immunized animals show neutralizing activity in all three adjuvant groups against HIV-SF2 and HIV-MN, both after four and after five immunizations. Six of 8 gp120-immunized animals also have significant neutralizing activity against HIV-HTLBIIIB, and the animals are from all three adjuvant groups.

TABLE 3

Neutralization Titers of Baboons Immunized with Env 2-3 (SF2)

| | | Neutralization titers[a] Virus Serum | | | | | |
|---|---|---|---|---|---|---|---|
| | Adju- | SF2 | | MN | | HTLVIIIB | |
| Animal | vant | Bleed7[c] | Bleed 12[d] | Bleed 5[b] | Bleed 12[d] | Bleed 5[B] | Bleed 12[d] |
| 2952 | 1[f] | 10 | 7.5 | 4 | 5 | 0 | 0 |
| 2957 | 1 | 20 | 20 | 0 | 1.8 | 0 | 0 |
| 2958 | 1 | 20 | 77 | 200 | 170 | 0 | 4.9 |
| 2950 | 2 | 6 | 0 | 0 | 0 | 0 | 0 |
| 2956 | 2 | 6.5 | 0 | 0 | 0 | 0 | 0 |
| 2967 | 2 | 12 | 4.5 | 0 | nt[e] | 0 | nt[e] |
| 2947 | 3 | 11 | nt[e] | 0 | 0 | 0 | 0 |
| 2948 | 3 | <4 | nt[e] | 0 | 0 | 0 | 0 |
| #positive/#animals | | 8/8 | 4/6 | 2/8 | 3/7 | 0/8 | 1/7 |
| Mean | | 11 | 18 | 26 | 25 | 0 | 0.7 |

[a]Neutralization assays were performed as follows: Virus stocks were titered for syncytial-forming units (SFU) on CEM-SS cells. Sera to be tested were heat-inactivated, diluted serially two-fold and mixed with 200 SFU for 1 hour at 37° C., then pipetted onto CEM-SS cells attached to microwells with poly-L-lysine for 1 hour at 37° C.. Virus-serum mixtures were then removed and the cells fed with medium. Syncytia formation was scored at 5 days post infection. Neutralization was scored by calculating Vn(# of syncytia formed in test wells) divided by Vo(# of syncytia in virus alone wells) for each dilution of test sera, and Vn/Vo was plotted as a function of serum dilution. Titers reported are the inverse of the dilution that gave Vn/Vo < 0.1 (>90% neutralization).
[b]Bleed 5 is at 10 weeks, two weeks following the third immunization.
[c]Bleed 7 is at 14 weeks, two weeks following the fourth immunization.
[d]Bleed 12 is at 23 weeks, three weeks following the fifth immunization.
[e]nt, not tested.
[f]Adjuvant 1 = IFA (incomplete Freund's Adjuvant) + 250 mg MTP-PE Adjuvant 2 = MF101 (250 mg MTP-PE) Adjuvant 3 = Alum

TABLE 4

Neutralization Titers of Baboons Immunized with gp120 (SF2)

| | | Neutralization titers[a] Virus Serum | | | | | |
|---|---|---|---|---|---|---|---|
| | Adju- | SF | | MN | | HTLVIIIB | |
| Animal | vant | Bleed 7[c] | Bleed 12[d] | Bleed 5[b] | Bleed 12[d] | Bleed 5[B] | Bleed 12[d] |
| 2951 | 1[e] | 40 | 160 | 140 | 128 | >2 | 55 |
| 2953 | 1 | 64 | 8 | 8 | 17 | 0 | 15 |
| 2964 | 1 | >64 | 230 | 80 | >256 | 7 | 82 |
| 2949 | 2 | 16 | 9.5 | 4.5 | 9.5 | 0 | 0 |
| 2954 | 2 | 16 | 13 | 8 | 24 | 0 | 0 |
| 2966 | 2 | 65 | 27 | 32 | 29 | 0 | 4 |
| 2955 | 3 | 16 | nt[e] | 5 | 40 | 0 | 15 |
| 2965 | 3 | 7 | nt[e] | 4 | 17 | 4.8 | 14 |
| #positive/ #animals | | 8/8 | 6/6 | 8/8 | 8/8 | 3/8 | 6/8 |
| Mean | | 36 | 75 | 35 | 65 | 1.7 | 23 |

[a]Neutralization assays were performed as described in Table 1.
[b]Bleed 5 is at 10 weeks, two weeks following the third immunization.
[c]Bleed 7 is at 14 weeks, two weeks following the fourth immunization.
[d]Bleed 12 is at 23 weeks, three weeks following the fifth immunization.
[e]Adjuvants were as described in Table 1.

Young adult (male/female) baboons (Papio) were immunized with 55 mg gp120 formulated in one of two adjuvants: aluminum hydroxide (alum, 0.8 mg per dose); or Incomplete Freund's Adjuvant plus 250 mg muramyl tripeptide (IFA-MTP). Animals were immunized approximately every four weeks and the sera were monitored for the loss of envelope-specific titer. Data summarizing the antigen-specific response for each animal in the study is set forth in Tables 5 and 6. Envelope specific titers peaked following each boost and then declined. Note that the alum and IFA-MTP titers differ by approximately ten-fold. Baseline titers were reached after six months of rest, and the animals were then reboosted at monthly intervals. To measure the effectiveness of the envelope antibodies in virus neutralization, sera were tested in in vitro neutralization assays against both homologous HIV-SF2 and heterologous virus isolates. Sera were tested at points of known high envelope titers for virus neutralization, at weeks 10 (after 3 immunizations), 23 (after 5 immunizations) before the rest, and at week 57 (after 6 immunizations) after the boost following the rest. Two virus neutralization assays were employed, a p24gag inhibition assay described in Haigwood et al., AIDS Res. Hum. Retrov. (1990) 6;855–869 and Steimer et al, Vaccine (1988), H. Gimsberg et al., Editor, Cold Spring Harbor Laboratory Press, p 347–355, and an infectious center inhibition assay by Nara et al., AIDS Res. Hum. Retrov. (1987), 3:283–302. As illustrated in Table 5, neutralizing antibodies effective against HIV-SF2 and HIV-MN were generated after only three immunizations in both adjuvant groups, and titers were maintained or increased with further boosting. In Table 6, HIV-BRU- and HIV-HTLVIIIB-specific neutralizing antibodies were reproducibly observed after five and six immunizations; no titers versus HIV-ZR6 were observed after six immunizations. Overall, both the homologous SF2 and the heterologous neutralizing titers were higher in the IFA-MTP animals than in the alum animals.

TABLE 5

Neutralization Titers of Immunized Baboons

| | | Neutralization titers Virus Serum | | | | | | | | |
|---|---|---|---|---|---|---|---|---|---|---|
| | | SF2 | | | | | MN | | | |
| | Adju-[g] | Bleed 5[c] | | Bleed 12[d] | | Bleed 22[e] | Bleed 5[d] | | Bleed 12[d] | Bleed 22[e] |
| Animal | vant | A[a] | B[b] | A | B | A | A | B | A | B | B |
| 2951 | 1 | 1,250 | nt[f] | 400 | 160 | 500 | 90 | 140 | 800 | 128 | 250 |
| 2953 | 1 | 500 | 50 | 475 | 8 | 2,300 | 35 | 8 | 175 | 17 | 100 |
| 2964 | 1 | 2,100 | 10 | 2,000 | 230 | 5,000 | 100 | 80 | 350 | 210 | 600 |
| 2955 | 2 | 300 | nt | 250 | nt | 160 | 50 | 5 | 200 | 40 | 28 |
| 2965 | 2 | 125 | nt | 350 | nt | 800 | —[h] | 4 | 50 | 17 | 21 |
| #positive/ #animals | | 5/5 | 2/3 | 5/5 | 3/3 | 5/5 | 4/5 | 5/5 | 5/5 | 5/5 | 5/5 |

[a]Assay performed by method of Steimer et al., 1988. Titers are the reciprocal of the greatest dilution to yield >50% inhibition of p25gag production.

TABLE 5-continued

Neutralization Titers of Immunized Baboons

| | | Neutralization titers Virus Serum | | | | | | | | |
|---|---|---|---|---|---|---|---|---|---|---|
| | | SF2 | | | | | MN | | | |
| | Adju-[g] | Bleed 5[c] | | Bleed 12[d] | | Bleed 22[e] | Bleed 5[d] | | Bleed 12[d] | Bleed 22[e] |
| Animal | vant | A[a] | B[b] | A | B | A | A | B | A | B | B |

[b]Assay performed by method of Nara et al., 1987. Titers are the reciprocal of the greatest dilution to yield >90% inhibition of infectious centers.
[c]Bleed 5 is at 10 weeks, two weeks following the third immunization.
[d]Bleed 12 is at 23 weeks, two weeks following the fifth immunization.
[e]Bleed 22 is at 57 weeks, two weeks following the sixth immunizataion.
[f]nt = not tested.
[g]Adjuvant 1 = IFA (incomplete Freund's Adjuvant) + 250 mg, MTP-PE Adjuvant 2 = Alum
[h]— indicates <10 for assay A; <4 for assay B

TABLE 6

Neutralization Titers of Baboons Immunized with gp120

| | | Neutralization Titers Virus Serum | | | | | | | | | |
|---|---|---|---|---|---|---|---|---|---|---|---|
| | | BRU | | | | | IIIB | | | Zr6 | | |
| | Adju-[g] | Bleed 5[d] | | Bleed 12[e] | | Bleed 22[f] | Bleed 5[d] | Bleed 12[e] | Bleed 22[f] | Bleed 5[d] | Bleed 12[e] | Bleed 22[f] |
| Animal | vant | A[a] | B[b] | A | B | B | B | B | B | B | B | B |
| 2951 | 1[e] | —[c] | — | 80 | — | 29 | — | 55 | 51 | — | — | — |
| 2953 | 1 | — | — | 20 | — | — | — | 15 | 6 | — | — | — |
| 2964 | 1 | — | — | 100 | 20 | 140 | 7 | 82 | 180 | — | — | — |
| 2955 | 2 | — | — | 15 | — | — | — | 15 | 11 | — | — | — |
| 2965 | 2 | — | — | — | — | — | 5 | 14 | 9 | — | — | — |
| #positive/ animals | | 0/5 | 0/5 | 4/5 | 1/5 | 2/5 | 2/5 | 5/5 | 5/5 | 0/5 | 0/5 | 0/5 |

[a]Assay performed by method of Steimer et al., 1988. Titers are the reciprocal of the greatest dilution to yield >50% inhibition of p25gag production.
[b]Assay performed by method of Nara et al., 1987. Titers are the reciprocal of the greatest dilution to yield >90% inhibition of infectious centers.
[c]— indicates <10 for assay A; <4 for assay B.
[d]Bleed 5 is at 10 weeks, two weeks following the third immunization.
[e]Bleed 12 is at 23 weeks, two weeks following the fifth immunization.
[f]Bleed 22 is at 57 weeks, two weeks following sixth immunization.
[g]Adjuvants were as described in Table 5.

Serum collected from the highest responding gp120-immunized baboon after six immunizations was further tested for the ability to neutralize additional virus isolates HIV-SF2, HIV-MN, HIV-RF, HIV-CC, HIV-ZR6, and HIV-NDK (Table 7a). Note that the HIV-SF2 neutralization titers were determined by the p24gag inhibition assay, while the HIV-MN neutralization was assayed by the Nara et al. infectious center protocol. Thus, the marked difference in neutralization of these two isolates can be accounted for, in part, by the two different assays used.

This data demonstrates that the gp120 protein retaining a material conformation is more successful in producing cross-neutralizing antibodies than forms that do not retain natural conformation.

EXAMPLE 7

Repeated immunization of the IFA-MTP group of baboons was carried out to determine if additional repeated exposure to recombinant, native, glycosylated gp120 might result in antibodies effective in neutralizing an even broader range of isolates. Repeated immunization did not drastically alter the titers of neutralizing antibodies against HIV-SF2, HIV-MN, HIV-RF, or HIV-CC. However, repeated immunization did result in the appearance of low titer neutralizing antibodies against African isolates, HIV-ZR6 and HIV-NDK (Table 7b). The temporal development of HIV-ZR6 neutralization was examined by graphing the virus neutralization data (FIG. 5) from Baboon 2964 Sera Analyzed after 0, 5, 6, 7, 8, and 9 immunizations with recombinant, native, glycosylated gp120.

Neutralization was scored by measuring the number of syncytial-forming units per ml (sfu/ml) in wells containing experimental sera (Vn, average of duplicate wells) and dividing this number by the sfu/ml virus alone (Vo, average of 8 replica wells). This fraction, Vn/Vo was plotted versus the dilution of the serum sample, and neutralization was scored by noting the dilution of serum which allowed a 90% reduction in Vn, i.e., Vn/Vo=0.1. Samples are indicated by the key on the right, where the numbers correspond to bleeds. Bleed 0 is the prebleed, which shows no virus neutralization. Bleed 12 follows 5 immunizations; bleed 22 follows 6 immunizations; bleed 24 follows 7 immunizations; bleed 27 follows 8 immunizations; bleed 22 follows 9 immunizations.

Figure 5A:
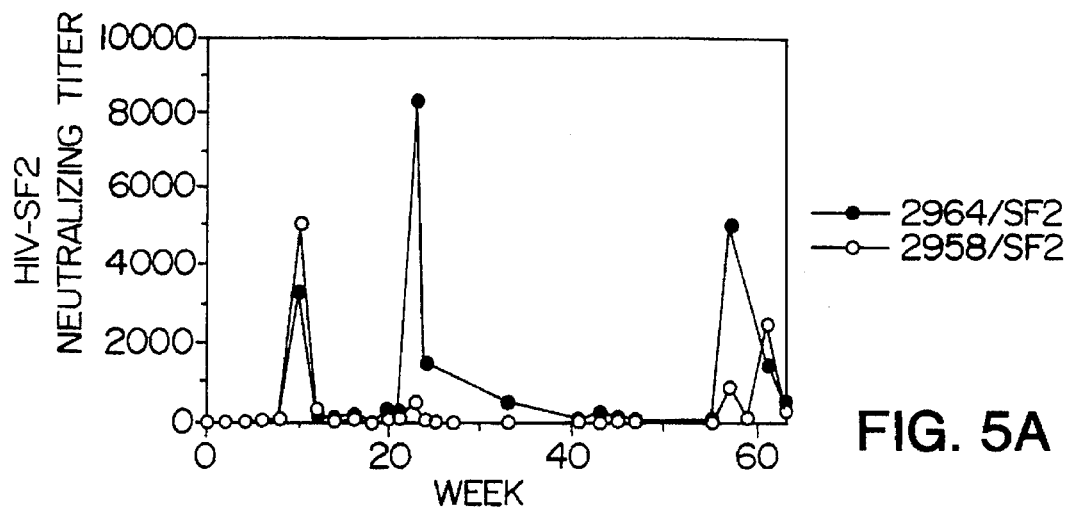
FIG. 5 is a graph showing HIV-ZR6 neutralization data from baboon 2964 sera analyzed after 0, 5, 6, 7, 8, and 9 immunizations with gp120.
Figure 5B:
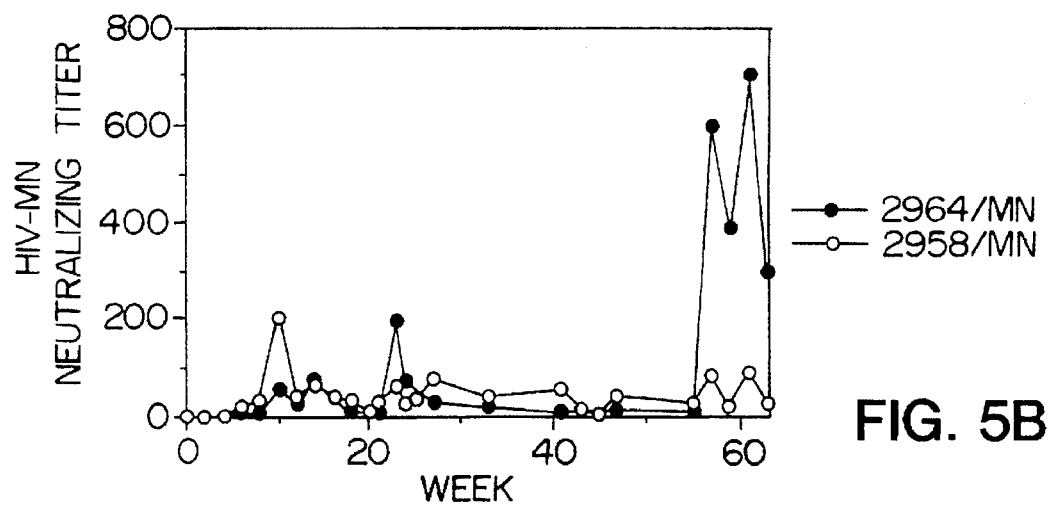
Figure 5C:
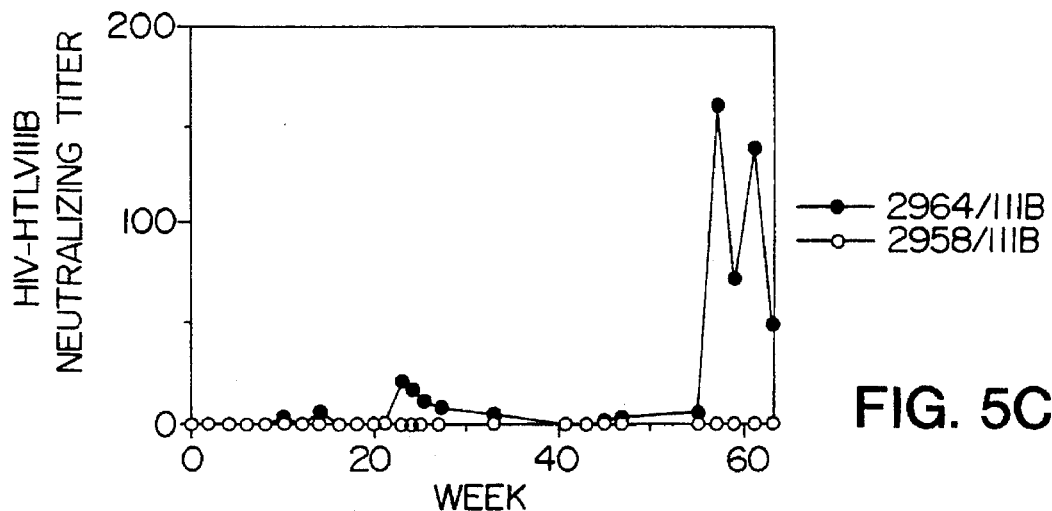

As is evident in FIG. 5, repeated boosting shifted the slope of the neutralization curve, so that neutralization was detected in bleed 32, following 9 immunizations. These results demonstrated that repeated boosting selected for antibody-producing clones that have broader specificity.

(data not shown); gp120 sera neutralized these three isolates as well as HIV-ZR6 after repeated boosting (Table 8).

Figure 6:
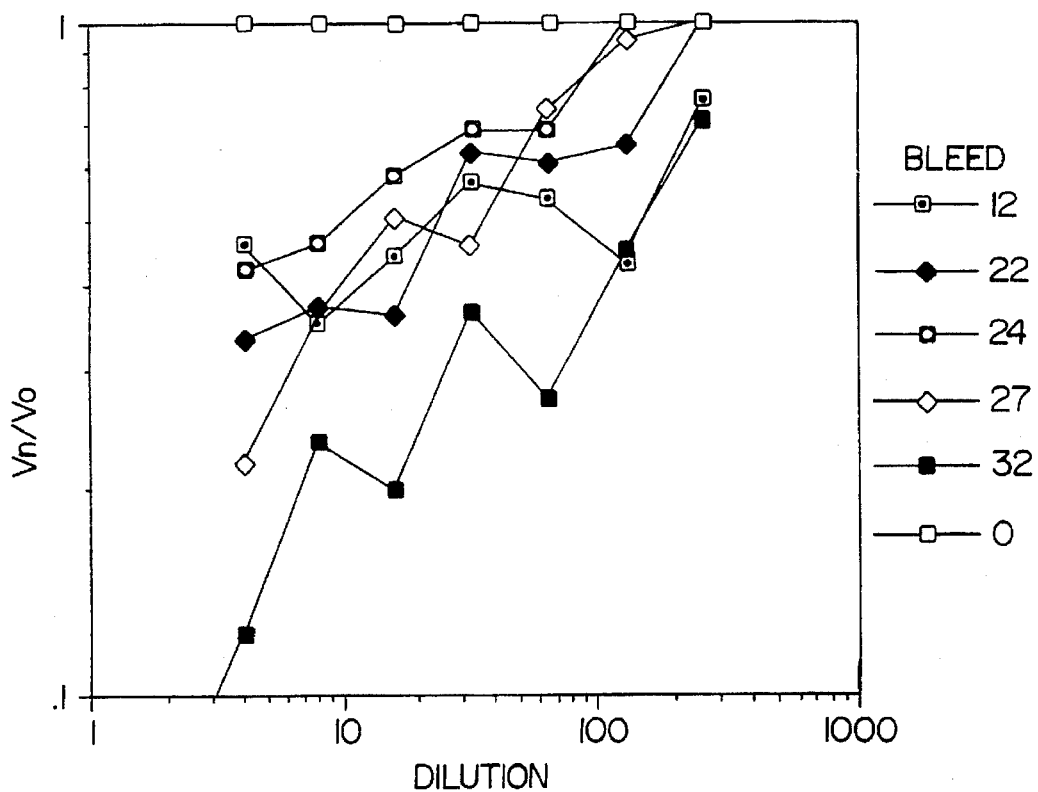
FIG. 6 is a set of graphs showing neutralization titers of all serum samples from Example 6 immunized baboon 2958 and gp120-immunized baboon 2964.

FIG. 6 is a set of graphs showing neutralization titers of all the serum samples from baboon 2958, immunized with denatured, non-glycosylated gp120, and baboon 2964, immunized with native, glycosylated gp120. Immunization of these animals is described in Example 6.

EXAMPLE 9

Baboons were immunized with 55 mg gp120 formulated with either: microfluidized emulsion containing muramyl TABLE 7a

| HIV-VIRUS | SF2 | MN | BRU | HTLVIIIB | HXB3 | V32 RF | CC | ZR6 |
|---|---|---|---|---|---|---|---|---|
| TITER | 5000 | 600 | 140 | 180 | 59 | 32 | 33 | 33 | <4 |

Results are of Bleed 22 at 57 weeks, two weeks after the sixth immunization using an assay performed by the method of Steiner et al., TABLE 7b Virus Neutralizing Titers for Baboon 2964 Following 6, 7, 8 and 9 Immunizations with gp120
Neutralization Titers

| Animal | Bleed | Immunization | HIV-SF2 | HIV-MN[a] | HIV-RF[b] | HIV-CC[b] | HIV-Zr6 | HIV-NDK[b] |
|---|---|---|---|---|---|---|---|---|
| 2964 | 22[e] | 6 | 5,000 | 600 | 33 | 33 | —[c] | nt[d] |
| 2964 | 24[f] | 7 | 1,500 | 700 | 21 | 10 | — | — |
| 2964 | 27[g] | 8 | 4,100 | 400 | 18 | 10 | — | 5 |
| 2964 | 32[h] | 9 | 7,000 | 310 | 18 | 6 | 4 | — |

[a]Bleeds 22 and 24 were tested on different days than bleeds 27 and 32.
[b]Bleeds 24, 27, and 12 were tested simultaneously; bleed 22 was tested on a different day.
[c]— indicates <10 for assay A; <4 for assay B.
[d]nt = not tested.
[e]Bleed 22 is at 57 weeks, two weeks following the sixth immunization.
[f]Bleed 24 is at 61 weeks, two weeks following the seventh immunization.
[g]Bleed 27 is at 67 weeks, two weeks following the eighth immunization.
[h]Bleed 32 is at 84 weeks, two weeks following the ninth immunization.

EXAMPLE 8

Analysis of all serum samples from two individual baboons, 2964 and 2958, further delineated differences in recombinant denatured, nonglycosylated protein and recombinant native, glycosylated (rgp120)-immunized animals (FIG. 6). Baboon 2964 was vaccinated with recombinant native glycosulated protein and baboon 2958 was vaccinated with recombinant, denatured, nongly-cosulated protein. HIV-SF2 neutralization was assayed by the p25gag inhibition assay described in Haigwood et al., AIDS. Res. and Hum. Retrov. (1990) 6:855–869. All other isolates were assayed by the infectious center inhibition assay. Serum from each bleed was assayed for virus neutralization activity against HIV-SF2, HIV-MN, and HIV-HTLVIIIB. Further boosting with denatured, nonglycosylated protein did not raise antibody or neutralization titers beyond the levels measured at week 10, and there was no detectable neutralization of HIV-HTLVIIIB. In the rgp120-immunized animal, HIV-SF2, HIV-MN, and HIV-HTLVIIIB titers increased following each boost, with the greatest increase observed following the rest. Patterns of neutralizing activity were similar for all three viruses, although response magnitudes differed. Emergence of HIV-HTLVIIIB neutralization was delayed relative to the other two isolates. In additional experiments in baboons discussed in Example 9 below, we have demonstrated that recombinant denatured, nonglycosylated protein formulated in MF59 was unable to induce neutralization to HIV-MN or HIV-BRU neutralizing activity tripeptide-phosphatidyl ethanolamine, 100 mg (MF59); or Incomplete Freund's Adjuvant (IFA). The formulation of MF59 was 5% squalene, 0.5% Tween-80, 0.5% Span-85 with endogenous MTP-PE at 0.4 mg/ml in water, which was emulsified with a microfluidized, and stored under argon until use. Then it was mixed with antigen by shaking and injected. Data summarizing the antigen-specific responses for the baboons are shown in Table 8.

Gp120-specific titers also peaked, then declined, following each boost in this study. Higher titers were achieved with MF59 than with IFA. Virus neutralization was tested versus homologous and heterologous isolates was determined at weeks 10, 24, and 38, following three, four, and five immunizations respectively. The results of these assays are summarized in Table 8. In this study, animals in the MF59 group had higher titers and a greater proportion of positive animals in the group than the IFA group. Neutralizing titers effective against HIV-SF2 and HIV-MN were observed after three immunizations, and against HIV-HTLVIIIB and HIV-ZR8 after five immunizations. The animals immunized with recombinant native, glycosylated gp120 in MF59 responded with antibodies that were effective in neutralizing HIV-BRU, and HIV-ZR6 after only five immunizations. In a previous study, neutralization of African isolates was achieved only after eight (HIV-NDK) or nine (HIV-ZR6) immunizations, In addition, the titers achieved in Example 9 with recombinant native, glycosylated gp120 adjuvanted with MF59 versus HIV-ZR6 were higher. Also, the appearance of neutralizing antibodies effective against HIV-BRU and HIV-ZR6 was simultaneous in this study, in contrast to Example 6 described above. This result could be due to the adjuvant or to the regimen immunizations, which allowed two shorter resting periods in Example compared with a single long resting period in Example 6.

and 36. Chimpanzees were immunized at weeks 0, 4, 8, and 28. The formulation of 2XMF59 was 10% squalene, 1% Tween-80, 1% Span-85 with endogenous MTP PE at 0.4 mg/ml in water, which was emulsified with a microfluidizer, and stored under argon until use, when it was mixed with

TABLE 8

Neutralization Titers of Immunized Baboons

| Animal | Adju-[h] vant | SF2[a] Bleed 5[e] | SF2[a] Bleed 12[f] | SF2[a] Bleed 14[g] | MN[b] Bleed 5[e] | MN[b] Bleed 12[f] | MN[b] Bleed 14[g] | BRU[b] Bleed 5[e] | BRU[b] Bleed 12[f] | BRU[b] Bleed 14[g] | Zr6[b] Bleed 5[e] | Zr6[b] Bleed 12[f] | Zr6[b] Bleed 14[g] |
|---|---|---|---|---|---|---|---|---|---|---|---|---|---|
| 46 | 1 | nt[c] | 70 | 110 | nt | 2 | 6 | nt | —[d] | 3 | — | — | — |
| 47 | 1 | 16 | 21 | 35 | — | — | 7 | — | — | — | — | — | — |
| 48 | 1 | 30 | 65 | 70 | 7 | 4 | 11 | — | — | 4 | — | — | — |
| 49 | 1 | 100 | 210 | 50 | — | 18 | 25 | — | — | — | — | — | 4 |
| 58 | 2 | 200 | 40 | 250 | — | 8 | 29 | — | — | 4 | — | — | — |
| 59 | 2 | 30 | 60 | 70 | 15 | 45 | 29 | — | — | 4 | — | — | 8 |
| 60 | 2 | 250 | 50 | 310 | 10 | 48 | 20 | — | — | 6 | — | — | — |
| 61 | 2 | 100 | 31 | 350 | 22 | 51 | 20 | — | — | 5 | — | — | 6 |
| 62 | 2 | 100 | 500 | 400 | 15 | 51 | 45 | — | — | 3 | — | — | 4 |
| #positive/ #animals | | 8/8 | 9/9 | 9/9 | 5/8 | 8/9 | 9/9 | 0/8 | 0/9 | 7/9 | 0/9 | 0/9 | 4/9 |

[a]Assay performed by method of Steimer et al., 1998. Titers are the reciprocal of the greatest dilution to yield >50% inhibition of p25gag production.
[b]Assay performed by method of Nara et al., 1987. Titers are the reciprocal of the greatest dilution to yield >90% inhibition of infectious centers.
[c]nt = not tested.
[d]— indicates <10 for assay a; <4 for assay b.
[e]Bleed 5 is at 10 weeks, two weeks following the third immunization.
[f]Bleed 12 is at 24 weeks, two weeks following the fourth immunization.
[g]Bleed 14 is at 38 weeks, three weeks following the fifth immunization.
[h]Adjuvant 1 = IFA (incomplete Freund's Adjuvant) + 250 mg MTP-PE Adjuvant 2 = MF59 (100 mg MTP-PE)

EXAMPLE 10

Figure 7:
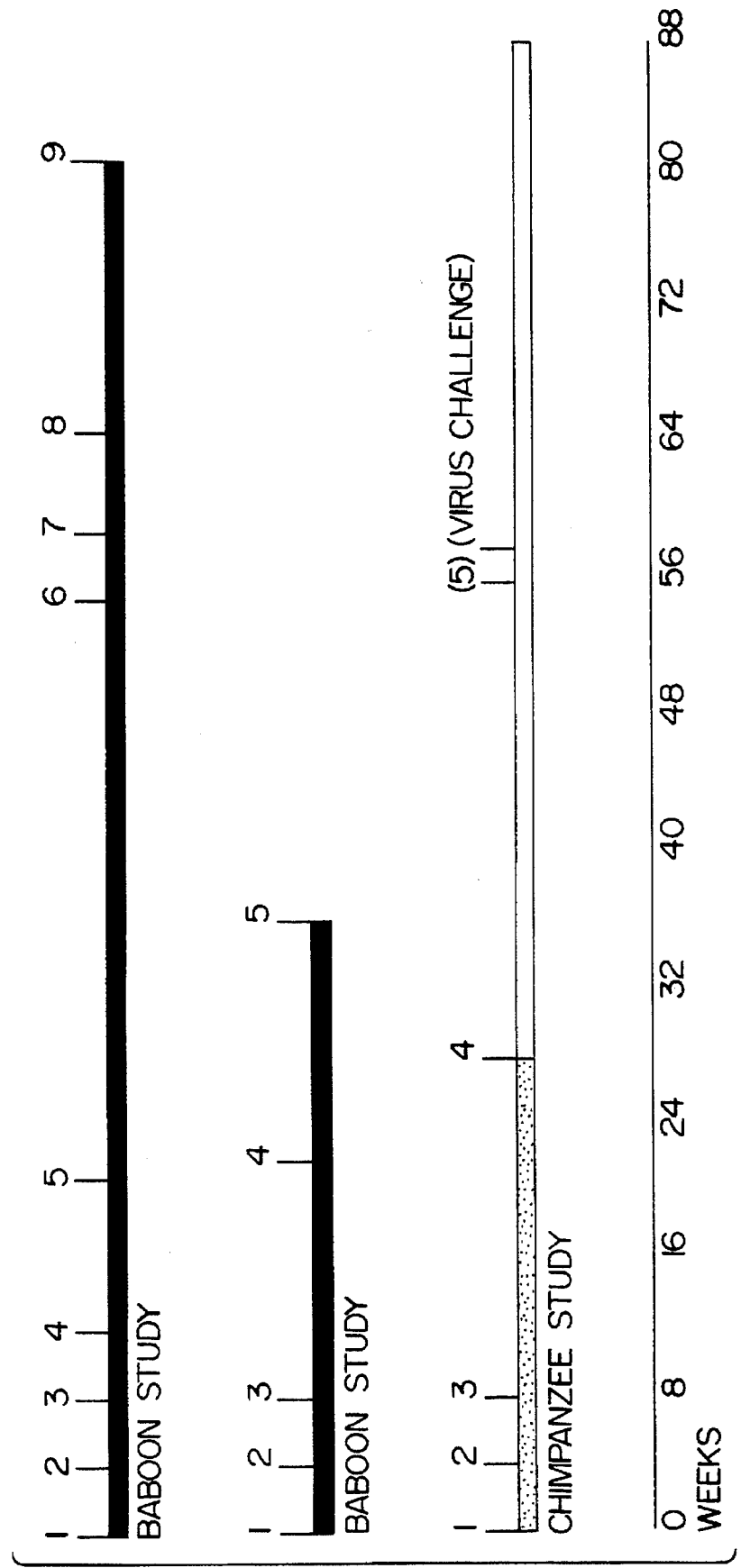
FIG. 7 is a schematic diagram of primate interrupted immunization regimen design.

Following procedures similar to those described above for baboons, four chimpanzees (*Pan troglodytes*) were immunized with 55 mg gp120 adjuvanted with 2XMF59 (2 animals), adjuvant alone (1 animal), or were unimmunized (1 animal), to determine the immunogenicity of the protein in this species of primates, man's closest living relative. The experimental regimen design is set forth in FIG. 7. In FIG. 7, the shaded bars represent time lines (immunization schedules) for each of three studies: baboons of Example 6 (top line), baboons of Example 9 (middle line), and chimpanzees of Example 10 (bottom line). A scale of time in weeks is shown at the bottom of the figure. Immunizations are indicated by vertical bars, numbered above to indicate the immunization number, at the position on the time line of the injection. Baboons in Example 6 were immunized at weeks 0, 4, 8, 12, 21, 55, 59, 65, and 80, except baboon 2964 which was immunized at week 82 instead of week 80. Baboons in Example 9 were immunized at weeks 0, 4, 8, 22, antigen by shaking and injected. The animals were immunized three times intramuscularly at monthly intervals, and sera have been analyzed for envelope-specific titers and for virus neutralizing antibodies for the bleeds following each immunization. The data are summarized in Table 9 for the two immunized with recombinant, native glycosylated chimpanzees. Neither of the other control chimpanzees developed gp120- specific antibodies or neutralizing antibodies (data not shown). Both animals immunized with recombinant native glycosylated protein have developed good responses to the immunizing antigen, and both animals have virus-neutralizing antibodies effective against HIV-SF2 and HIV-MN. Serum from one of the chimpanzees also neutralized HIV-HTLVIIIB following three immunizations. The chimpanzees are boosted following a six month rest period, and sera are analyzed following this immunization. When the virus neutralizing titers against HIV-SF2 are sufficiently high, the animals are challenged with a chimpanzee-titered stock of HIV-SF2. The chimpanzees are re-immunized two weeks prior to challenge. Given the existence of neutralizing antibodies effective against heterologous isolates, the possibility for heterologous virus challenge in these same animals also exists.

TABLE 9

Neutralization Titers of Chimpanzees Immunized with 2X MF-59 (gp120 Animals)

| Animal | Bleed | Immunization | Virus Isolate: Assay: ELISA Titer | Neutralization titers | | | |
| --- | --- | --- | --- | --- | --- | --- | --- |
| | | | | SF2 A[a] | MN A | MN B[b] | IIIB B |
| 10143 | 0 | 0 | <100 | —[c] | — | — | — |
| 10143 | 1 | 1 | <100 | nt[d] | nt | — | — |
| 10143 | 2 | 2 | 5,800 | 60 | — | — | — |
| 10143 | 4 | 3 | 15,700 | 280 | — | 15 | — |
| 10144 | 0 | 0 | <100 | — | — | — | — |
| 10144 | 1 | 1 | <100 | nt | nt | — | — |
| 10144 | 2 | 2 | 11,000 | 25 | — | — | — |
| 10144 | 4 | 3 | 52,600 | 400 | 72 | 40 | 7 |
| #positive/ #animals | | | 2/2 | 2/2 | 1/2 | 2/2 | 1/2 |

[a] Assay A performed by the method of Steimer et al., 1988.
[b] Assay B performed by the method of Nara et al., 1987.
[c] — indicates <10 for assay A; <2 for assay B
[d] nt = not tested.

The invention now being fully described, it will be apparent to one of ordinary skill in the art that many changes and modifications can be made thereto without departing from the spirit or scope of the appended claims.

Deposit of Biological Materials

The following exemplary materials have been deposited on Nov. 7, 1990, with the American Type Culture Collection (ATCC), Rockville, Md, and designated as indicated. These deposits will be maintained under the terms of the Budapest Treaty on the International Recognition of the Deposit of Micro-organisms for purposes of patent procedures.

| Deposit | ATCC # | Deposited |
| --- | --- | --- |
| Chinese Hamster Ovary Cells CHO-A-6a120-145-0.1-22 | CRL 10379 | March 9, 1990 |
| Chinese Hamster Ovary Cells CHO-DG44 | CRL 10378 | March 8, 1990 |
| E. coli HB101 (pCMV6a120-SF2) | 68249 | March 8, 1990 |

These deposits are provided merely as convenience to those of skill in the art, and are not an admission that a deposit is required under 35 U.S.C. 112. The nucleic acid sequences of these plasmids, as well as the amino acid sequences of the polypeptides encoded thereby, are incorporated herein by reference and are controlling in the event of any conflict with the description herein. A license may be required to make, use, or sell the deposited materials, and no such license is hereby granted.

What is claimed is:

1. A method for stimulating the formation of antibodies capable of neutralizing infection by an HIV viral isolate in at least one mammalian species, which comprises immunizing a mammalian subject with an antigenic composition containing purified, full-length, non-fusion recombinant HIV gp120 glycoprotein having protein/protein-interaction properties substantially identical to gp120 as presented on an HIV virus.

2. The method of claim 1, wherein said mammal is a primate.

3. The method of claim 1 wherein the protein/protein-interaction properties of the glycoprotein comprise:
   (a) binding affinity for CD4;
   (b) binding affinity for an antibody capable of neutralizing HIV infectivity; or
   (c) binding affinity for gp41.

4. The method of claim 1 wherein the composition further comprises an adjuvant.

5. The method of claim 4 wherein the adjuvant is an aluminum salt.

6. The method of claim 4 wherein the adjuvant is an oil-in-water emulsion formed from a metabolizable oil and an emulsifying agent.

7. The method of claim 1 wherein the composition comprises at least about 1 mg of the glycoprotein.

8. The method of claim 7 wherein the composition is suspended in a volume of a pharmaceutical vehicle or carrier.

9. The method of claim 8 wherein the volume of the pharmaceutical vehicle or carrier is about 0.1 to 1.0 mL.

10. The method of claim 9 wherein the composition is administered to the mammalian subject by injection.

* * * * *